US007201908B2

(12) United States Patent
Cid-Arregui et al.

(10) Patent No.: US 7,201,908 B2
(45) Date of Patent: Apr. 10, 2007

(54) MODIFIED HPV E6 AND E7 GENES AND PROTEINS USEFUL FOR VACCINATION

(75) Inventors: Angel Cid-Arregui, Heidelberg (DE); Harald Zur Hausen, Waldmichelbach (DE)

(73) Assignee: Deutsches Krebsforschungszentrum Stiftung Des Offentlichen Rechts (DE)

( * ) Notice: Subject to any disclaimer, the term of this patent is extended or adjusted under 35 U.S.C. 154(b) by 28 days.

(21) Appl. No.: 10/472,724

(22) PCT Filed: Mar. 22, 2002

(86) PCT No.: PCT/EP02/03271

§ 371 (c)(1), (2), (4) Date: Jan. 29, 2004

(87) PCT Pub. No.: WO02/081709

PCT Pub. Date: Oct. 17, 2002

(65) Prior Publication Data

US 2004/0171806 A1 Sep. 2, 2004

(30) Foreign Application Priority Data

Mar. 23, 2001 (EP) .................................. 01107271

(51) Int. Cl.
*A61K 39/12* (2006.01)

(52) U.S. Cl. ...................... 424/204.1; 435/6; 435/69.1; 530/300

(58) Field of Classification Search ............. 424/204.1; 435/6, 69.1, 235.1; 530/300
See application file for complete search history.

(56) References Cited

FOREIGN PATENT DOCUMENTS

| | | | |
|---|---|---|---|
| EP | 0 271 302 A2 | | 6/1988 |
| WO | WO 99/10375 | | 4/1999 |
| WO | WO 99/55876 | * | 11/1999 |
| WO | WO 01/14416 A2 | * | 3/2001 |
| WO | WO 01/17551 A2 | * | 3/2001 |

OTHER PUBLICATIONS

Smahel, Michal, et al., "Modified HVPV16 E7 Genes as DNA Vaccine Against E-7-Containing Oncogenic Cells", Virology 281, 231-238 (2001).

Boursnell, M.E.G., et al., "Construction and characterization of a recombinant vaccinia virus expressing human papillomavirus proteins for immunotherapy of cervical cancer", Vaccine, vol. 14, No. 16, patent. 1485-1494 (1996).

Lipari, Francesco, et al., "Purification and Biophysucal Characterization of a Minimal Functional Domain and of an N-Terminal $Zn^{2+}$-Binding Fragment from the Human Papillomavirus Type 16 E6 Protein", Biochemistry 2001, 40, 1196-1204 (2001).

Zhou, Jian, et al., Papillomavirus Capsid Protein Exprssion Level Depends on the Match between Codon Usage and tRNA Availabiality, Journal of Virology, 4972-4982, (Jun. 1999).

Smahel, Michal, et al. "Modified HPV 16 E7 Genes as DNA Vaccine against E7-Containing Oncogenic Cells." Virology, (2001), vol. 281, pp. 231-238.

Daemen, Toos, et al. "Eradication of established HPV 16-transformed tumours after immunisation with recombinant Semliki Forest virus expressing a fusion protein of E6 and E7." Vaccine, (2003), vol. 21, pp. 1082-1088.

Liu, Wen Jun, et al. "Codon Modified Human Papillomavirus Type 16 E7 DNA Vaccine Enhances Cytotoxic T-Lymphocyte Induction and Anti-tumor Activity." Virology, (2002), vol. 301, pp. 43-52.

* cited by examiner

*Primary Examiner*—Ali R. Salimi
(74) *Attorney, Agent, or Firm*—Steven J. Hultquist; Intellectual Property/Technology Law

(57) ABSTRACT

Described are DNA sequences encoding an E6 or E7 fusion-protein of HPV, wherein said DNA sequences are characterized by a combination of the following features: original codons are exchanged by codons which lead to an enhanced translation in a mammalian cell, they contain a deletion resulting in the production of a truncated non-functional protein, and they encode a fusionpartner which is a highly immunogenic polypeptide capable of enhancing the immunogenicity of the E6 or E7 protein in the mammalian host. Furthermore, the modified E6 or E7 protein encoded by said DNA sequences as well as expression vectors containing said DNA sequences are described as well as several uses of the these compounds.

19 Claims, 13 Drawing Sheets

CAAGCTTGCTAGC

ATG CAC CAC CAC CAC CAC CAC GGC GAC ACC CCC ACC TTG CAC GAG
M H H H H H H G D T P T L H E

TAC ATG TTG GAC TTG CAG CCC GAG ACC ACC GAC CTG TAC TGC TAC
Y M L D L Q P E T T D L Y C Y

GAG CAG TTG AAC GAC AGC TCC GAG GAG GAG GAC GAG ATC GAC GGC
E Q L N D S S E E E D E I D G

CCC GCC GGC CAG GCC GAG CCC GAC CGC GCC CAC TAC AAC ATC GTG
P A G Q A E P D R A H Y N I V

ACC TTC TGC TGC AAG TGC GAC TCC ACC CTG CGC CTG TGC GTG CAG
T F C C K C D S T L R L C V Q

AGC ACC CAC GTG GAC ATC CGC ACC TTG GAG GAC CTG CTG ATG GGC
S T H V D I R T L E D L L M G

ACC CTG GGC ATC GTG TGC CCC ATC TGC AGC CAG AAG CCC GAC TAC
T L G I V C P I C S Q K P D Y

AAG GAC GAC GAC GAC AAG TAA GAATTCGGATCCG
K D D D D K *

FIG. 1

CAAGCTTGCTAGC

ATG CAC CAC CAC CAC CAC CAC CAG AAG CGC ACC GCC ATG TTC CAG
M H H H H H H Q K R T A M F Q

GAC CCC CAG GAG CGC CCC CGC AAG CTG CCC CAG CTG TGC ACC GAG
D P Q E R P R K L P Q L C T E

CTG CAG ACC ACC ATC CAC GAC ATC ATC CTG GAG TGC GTG TAC TGC
L Q T T I H D I I L E C V Y C

AAG CAG CAG CTG CTG CGC CGC GAG GTG TAC GAC TTC GCC TTC CGC
K Q Q L L R R E V Y D F A F R

GAC CTG TGC ATC GTG TAC CGC GAC GGC AAC CCC TAC GCC GTG TGC
D L C I V Y R D G N P Y A V C

GAC AAG TGC CTG AAG TTC TAC TCC AAG ATC AGC GAG TAC CGC CAC
D K C L K F Y S K I S E Y R H

TAC TGC TAC AGC CTG TAC GGC ACC ACC CTG GAG CAG CAG TAC AAC
Y C Y S L Y G T T L E Q Q Y N

AAG CCC CTG TGC GAC CTG CTG ATC CGC TGC ATC AAC TGC CAG AAG
K P L C D L L I R C I N C Q K

CCC CTG TGC CCC GAG GAG AAG CAG CGC CAC CTG GAC AAG AAG CAG
P L C P E E K Q R H L D K K Q

CGC TTC CAC AAC ATC AGG GGC CGG TGG ACC GGG CGC TGC ATG TCC
R F H N I R G R W T G R C M S

TGC TGC CGC TCC TCC CGC ACC CGC CGC GAG ACC CAG CTG GAC TAC
C C R S S R T R R E T Q L D Y

AAG GAC GAC GAC GAC AAG TAA GAATTCGGATCCG
K D D D D K *

FIG. 2

```
                                                      CAAGCTTGCTAGC
ATG CAC CAC CAC CAC CAC CAC GGC CCC AAG GCC ACC CTG CAG GAC
M   H   H   H   H   H   H   G   P   K   A   T   L   Q   D

ATC GTG CTG CAC CTG GAG CCC CAG AAC GAG ATC CCC GTG GAC CTG
I   V   L   H   L   E   P   Q   N   E   I   P   V   D   L

CTG TGC CAC GAG CAG CTG AGC GAC TCC GAG GAG GAG AAC GAC GAG
L   C   H   E   Q   L   S   D   S   E   E   E   N   D   E

ATC GAC GGC GTG AAC CAC CAG CAC CTG CCC GCC CGC CGG GCC GAG
I   D   G   V   N   H   Q   H   L   P   A   R   R   A   E

CCC CAG CGC CAC ACC ATG CTG TGC ATG TGC TGC AAG TGC GAG GCC
P   Q   R   H   T   M   L   C   M   C   C   K   C   E   A

CGC ATC GAG CTG GTG GTG GAG AGC TCC GCC GAC GAC CTG CGC GCC
R   I   E   L   V   V   E   S   S   A   D   D   L   R   A

TTC CAG CAG CTG TTC CTG AAC ACC CTG TCC TTC GTG TGC CCC TGG
F   Q   Q   L   F   L   N   T   L   S   F   V   C   P   W

TGC GCC TCC CAG CAG GAC TAC AAG GAC GAC GAC GAC AAG TAA
C   A   S   Q   Q   D   Y   K   D   D   D   D   K   *

GAATTCGGATCCG
```

FIG. 3

CAAGCTTGCTAGC

ATG CAC CAC CAC CAC CAC CAC GCC CGC TTC GAG GAC CCC ACC CGC
M H H H H H H A R F E D P T R

CGC CCC TAC AAG CTG CCC GAC CTG TGC ACC GAG CTG AAC ACC TCC
R P Y K L P D L C T E L N T S

CTG CAG GAC ATC GAG ATC ACC TGC GTG TAC TGC AAG ACC GTG CTG
L Q D I E I T C V Y C K T V L

GAG CTG ACC GAG GTG TTC GAG TTC GCC TTC AAG GAC CTG TTC GTG
E L T E V F E F A F K D L F V

GTG TAC CGC GAC AGC ATC CCC CAC GCC GCC TGC CAC AAG TGC ATC
V Y R D S I P H A A C H K C I

GAC TTC TAC AGC CGC ATC CGC GAG CTG CGC CAC TAC TCC GAC TCC
D F Y S R I R E L R H Y S D S

GTG TAC GGC GAC ACC CTG GAG AAG CTG ACC AAC ACC GGC CTG TAC
V Y G D T L E K L T N T G L Y

AAC CTG CTG ATC CGC TGC CTG CGC TGC CAG AAG CCC CTG AAC CCC
N L L I R C L R C Q K P L N P

GCC GAG AAG CTG CGC CAC CTG AAC GAG AAG CGC CGC TTC CAC AAC
A E K L R H L N E K R R F H N

ATC GCC GGC CAC TAC CGC GGC CAG TGC CAC TCC TGC TGC AAC CGC
I A G H Y R G Q C H S C C N R

GCC CGC CAG GAG CGC CTG CAG CGC CGC CGC GAG ACC CAG GTG GAC
A R Q E R L Q R R R E T Q V D

TAC AAG GAC GAC GAC GAC AAG TAA GAATTCGGATCCG
Y K D D D D K *

FIG. 4

CGT TTC TCC TGG CTC AGT TTA CTA GTG CCA TTT GTT CAG TGG TTC
R F S W L S L L V P F V Q W F

GTA GGG CTT TCC CCC ACT GTT TGG CTT TCA GTT ATA TGG ATG ATG
V G L S P T V W L S V I W M M

TGG TAT TGG GGG CCA AGT CTG TAC AGC ATC TTG AGT CCC TTT TTA
W Y W G P S L Y S I L S P F L

CCG CTG TTA CCA ATT TTC TTT TGT CTT TGG GTA TAC ATT GAT ATC
P L L P I F F C L W V Y I D I

...

ATG CAC GGC GAC ACC CCC ACC TTG CAC GAG TAC ATG TTG GAC TTG
M H G D T P T L H E Y M L D L

CAG CCC GAG ACC ACC GAC CTG TAC TGC TAC GAG CAG TTG AAC GAC
Q P E T T D L Y C Y E Q L N D

AGC TCC GAG GAG GAG GAC GAG ATC GAC GGC CCC GCC GGC CAG GCC
S S E E E D E I D G P A G Q A

GAG CCC GAC CGC GCC CAC TAC AAC ATC GTG ACC TTC TGC TGC AAG
E P D R A H Y N I V T F C C K

TGC GAC TCC ACC CTG CGC CTG TGC GTG CAG AGC ACC CAC GTG GAC
C D S T L R L C V Q S T H V D

ATC CGC ACC TTG GAG GAC CTG CTG ATG GGC ACC CTG GGC ATC GTG
I R T L E D L L M G T L G I V

TGC CCC ATC TGC AGC CAG AAG CCC GAC TAC AAG GAC GAC GAC GAC
C P I C S Q K P D Y K D D D D

AAG TAA GAATTCGGATCCG 3'
K *

FIG. 5A

```
                              5' CTCGAGGATTGGGGACCCTGCGCTGAAC      ATG GAG AAC
                                                                    M   E   N

ATC ACA TCA GGA TTC CTA GGA CCC CTT CTC GTG TTA CAG GCG GGG
I   T   S   G   F   L   G   P   L   L   V   L   Q   A   G

TTT TTC TTG TTG ACA AGA ATC CTC ACA ATA CCG CAG AGT CTA GAC
F   F   L   L   T   R   I   L   T   I   P   Q   S   L   D

TCG TGG TGG ACT TCT CTC AAT TTT CTA GGG GGA ACT ACC GTG TGT
S   W   W   T   S   L   N   F   L   G   G   T   T   V   C

CTT GGC CAA AAT TCG CAG TCC CCA ACC TCC AAT CAC TCA CCA ACC
L   G   Q   N   S   Q   S   P   T   S   N   H   S   P   T

TCT TGT CCT CCA ACT TGT CCT GGT TAT CGC TGG ATG TGT CTG CGG
S   C   P   P   T   C   P   G   Y   R   W   M   C   L   R

CGT TTT ATC ATC TTC CTC TTC ATC CTG CTG CTA TGC CTC ATC TTC
R   F   I   I   F   L   F   I   L   L   L   C   L   I   F

TTG TTG GTT CTT CTG GAC TAT CAA GGT ATG TTG CCC GTT TGT CCT
L   L   V   L   L   D   Y   Q   G   M   L   P   V   C   P

CTA ATT CCA GGA TCC TCA ACA ACC AGC ACG GGA CCA TGC CGG ACC
L   I   P   G   S   S   T   T   S   T   G   P   C   R   T

TGC ATG ACT ACT GCT CAA GGA ACC TCT ATG TAT CCC TCC TGT TGC
C   M   T   T   A   Q   T   T   S   M   Y   P   S   C   C

TGT ACC AAA CCT TCG GAC GGA AAT TGC ACC TGT ATT CCC ATC CCA
C   T   K   P   S   D   G   N   C   T   C   I   P   I   P

TCA TCC TGG GCT TTC GGA AAA TTC CTA TGG GAG TGG GCC TCA GCC
S   S   W   A   F   G   K   F   L   W   E   W   A   S   A
```

FIG. 5B

```
 2/1                                                 29/1
c tcg agg att ggg gac cct gcg ctg aac atg gag aac atc acC tcC ggC ttc ctG ggC ccc
                                      M   E   N   I   T   S   G   F   L   G   P
62/12                                   92/22
ctG ctG gtg CTG cag gcC ggC ttC ttc Ctg Ctg acC CgC atc ctG acC atC ccC cag agC
L   L   V   L   Q   A   G   F   F   L   L   T   R   I   L   T   I   P   Q   S
122/32                                  152/42
ctG gac tcC tgg tgg acC tcC ctG aaC ttC ctG ggC ggC acC acc gtg tgC ctG ggc caG
L   D   S   W   W   T   S   L   N   F   L   G   G   T   T   V   C   L   G   Q
182/52                                  212/62
aaC tcC cag tcc ccC acc tcc aaC cac tcC ccC acc tcC tgC ccC ccC acC tgC ccC ggC
N   S   Q   S   P   T   S   N   H   S   P   T   S   C   P   P   T   C   P   G
242/72                                  272/82
taC cgc tgg atg tgC ctg cgC cgC ttC atc atc ttc ctG ttc atc ctg ctg ctG tgc ctG
Y   R   W   M   C   L   R   R   F   I   I   F   L   F   I   L   L   L   C   L
302/92                                  332/102
atc ttc Ctg Ctg gtG ctG ctg gac taC caG ggC atg Ctg ccc gtG tgC ccC ctG atC ccC
I   F   L   L   V   L   L   D   Y   Q   G   M   L   P   V   C   P   L   I   P
362/112                                 392/122
ggC tcc AGC acC acc agc acC ggC ccC tgc cgC acc tgc atg acC acC gcC caG ggC acc
G   S   S   T   T   S   T   G   P   C   R   T   C   M   T   T   A   Q   G   T
422/132                                 452/142
tcC atg taC ccc tcc tgC tgc tgC acc aaG ccC AGC gac ggC aaC tgc acc tgC atC ccc
S   M   Y   P   S   C   C   C   T   K   P   S   D   G   N   C   T   C   I   P
482/152                                 512/162
atc ccC AGC tcc tgg gcC ttc ggC aaG ttc ctG tgg gag tgg gcc AGC gcc cgC ttc AGC
I   P   S   S   W   A   F   G   K   F   L   W   E   W   A   S   A   R   F   S
542/172                                 572/182
tgg ctG agC CtG ctG gtg ccC ttC gtG cag tgg ttc gtG ggC ctG AGc ccc acC gtG tgg
W   L   S   L   L   V   P   F   V   Q   W   F   V   G   L   S   P   T   V   W
602/192                                 632/202
ctG AGC gtG atC tgg atg atg tgg taC tgg ggC ccC agC ctg tac agc atc Ctg agC ccc
L   S   V   I   W   M   M   W   Y   W   G   P   S   L   Y   S   I   L   S   P
662/212                                 692/222
ttC CtG ccC ctg CtG ccC atC ttc ttC tgC ctG tgg gtG tac atC gat atc taa
F   L   P   L   L   P   I   F   F   C   L   W   V   Y   I   D   I   *
```

FIG. 8

```
1                                         29/1
CTCG AGG ATT GGG GAC CCT GCG CTG AAC ATG GAG AAC ATC ACA TCA GGA TTC CTA GGA CCC
                                     M   E   N   I   T   S   G   F   L   G   P
62/12                                    92/22
CTT CTC GTG TTA CAG GCG GGG TTT TTC TTG TTG ACA AGA ATC CTC ACA ATA CCG CAG AGT
L   L   V   L   Q   A   G   F   F   L   L   T   R   I   L   T   I   P   Q   S
122/32                                   152/42
CTA GAC TCG TGG TGG ACT TCT CTC AAT TTT CTA GGG GGA ACT ACC GTG TGT CTT GGC CAA
L   D   S   W   W   T   S   L   N   F   L   G   G   T   T   V   C   L   G   Q
182/52                                   212/62
AAT TCG CAG TCC CCA ACC TCC AAT CAC TCA CCA ACC TCT TGT CCT CCA ACT TGT CCT GGT
N   S   Q   S   P   T   S   N   H   S   P   T   S   C   P   P   T   C   P   G
242/72                                   272/82
TAT CGC TGG ATG TGT CTG CGG CGT TTT ATC ATC TTC CTC TTC ATC CTG CTG CTA TGC CTC
Y   R   W   M   C   L   R   R   F   I   I   F   L   F   I   L   L   L   C   L
302/92                                   332/102
ATC TTC TTG TTG GTT CTT CTG GAC TAT CAA GGT ATG TTG CCC GTT TGT CCT CTA ATT CCA
I   F   L   L   V   L   L   D   Y   Q   G   M   L   P   V   C   P   L   I   P
362/112                                  392/122
GGA TCC TCA ACA ACC AGC ACG GGA CCA TGC CGG ACC TGC ATG ACT ACT GCT CAA GGA ACC
G   S   S   T   T   S   T   G   P   C   R   T   C   M   T   T   A   Q   G   T
422/132                                  452/142
TCT ATG TAT CCC TCC TGT TGC TGT ACC AAA CCT TCG GAC GGA AAT TGC ACC TGT ATT CCC
S   M   Y   P   S   C   C   C   T   K   P   S   D   G   N   C   T   C   I   P
482/152                                  512/162
ATC CCA TCA TCC TGG GCT TTC GGA AAA TTC CTA TGG GAG TGG GCC TCA GCC CGT TTC TCC
I   P   S   S   W   A   F   G   K   F   L   W   E   W   A   S   A   R   F   S
542/172                                  572/182
TGG CTC AGT TTA CTA GTG CCA TTT GTT CAG TGG TTC GTA GGG CTT TCC CCC ACT GTT TGG
W   L   S   L   L   V   P   F   V   Q   W   F   V   G   L   S   P   T   V   W
602/192                                  632/202
CTT TCA GTT ATA TGG ATG ATG TGG TAT TGG GGG CCA AGT CTG TAC AGC ATC TTG AGT CCC
L   S   V   I   W   M   M   W   Y   W   G   P   S   L   Y   S   I   L   S   P
662/212                                  692/222
TTT TTA CCG CTG TTA CCA ATT TTC TTT TGT CTT TGG GTA TAC ATT GAT ATC ATG CAC GGC
F   L   P   L   L   P   I   F   F   C   L   W   V   Y   I   D   I   M   H   G
722/232                                  752/242
GAC ACC CCC ACC TTG CAC GAG TAC ATG TTG GAC TTG CAG CCC GAG ACC ACC GAC CTG TAC
D   T   P   T   L   H   E   Y   M   L   D   L   Q   P   E   T   T   D   L   Y
782/252                                  812/262
TGC TAC GAG CAG TTG AAC GAC AGC TCC GAG GAG GAG GAC GAG ATC GAC GGC CCC GCC GGC
C   Y   E   Q   L   N   D   S   S   E   E   E   D   E   I   D   G   P   A   G
842/272                                  872/282
CAG GCC GAG CCC GAC CGC GCC CAC TAC AAC ATC GTG ACC TTC TGC TGC AAG TGC GAC TCC
Q   A   E   P   D   R   A   H   Y   N   I   V   T   F   C   C   K   C   D   S
902/292                                  932/302
ACC CTG CGC CTG TGC GTG CAG AGC ACC CAC GTG GAC ATC CGC ACC TTG GAG GAC CTG CTG
T   L   R   L   C   V   Q   S   T   H   V   D   I   R   T   L   E   D   L   L
962/312                                  992/322
ATG GGC ACC CTG GGC ATC GTG TGC CCC ATC TGC AGC CAG AAG CCC GAC TAC AAG GAC GAC
M   G   T   L   G   I   V   C   P   I   C   S   Q   K   P   D   Y   K   D   D
1022/332
GAC GAC AAG TAA GAA TTC GGA TCC G
D   D   K   *
```

FIG. 9

SEQUENCE LISTING

```
<160> NUMBER OF SEQ ID NOS: 27

<210> SEQ ID NO 1
<211> LENGTH: 542
<212> TYPE: DNA
<213> ORGANISM: Artificial Sequence
<220> FEATURE:
<223> OTHER INFORMATION: Mutagenized E6 gene of HPV-16
<220> FEATURE:
<221> NAME/KEY: CDS
<222> LOCATION: (14)..(526)

<400> SEQUENCE: 1

caagcttgct agc atg cac cac cac cac cac cac cag aag cgc acc gcc       49
               Met His His His His His His Gln Lys Arg Thr Ala
               1               5                   10

atg ttc cag gac ccc cag gag cgc ccc cgc aag ctg ccc cag ctg tgc       97
Met Phe Gln Asp Pro Gln Glu Arg Pro Arg Lys Leu Pro Gln Leu Cys
        15                  20                  25

acc gag ctg cag acc acc atc cac gac atc atc ctg gag tgc gtg tac      145
Thr Glu Leu Gln Thr Thr Ile His Asp Ile Ile Leu Glu Cys Val Tyr
    30                  35                  40

tgc aag cag cag ctg ctg cgc cgc gag gtg tac gac ttc gcc ttc cgc      193
Cys Lys Gln Gln Leu Leu Arg Arg Glu Val Tyr Asp Phe Ala Phe Arg
45                  50                  55                  60

gac ctg tgc atc gtg tac cgc gac ggc aac ccc tac gcc gtg tgc gac      241
Asp Leu Cys Ile Val Tyr Arg Asp Gly Asn Pro Tyr Ala Val Cys Asp
                65                  70                  75

aag tgc ctg aag ttc tac tcc aag atc agc gag tac cgc cac tac tgc      289
Lys Cys Leu Lys Phe Tyr Ser Lys Ile Ser Glu Tyr Arg His Tyr Cys
            80                  85                  90
```

-continued

```
tac agc ctg tac ggc acc acc ctg gag cag cag tac aac aag ccc ctg      337
Tyr Ser Leu Tyr Gly Thr Thr Leu Glu Gln Gln Tyr Asn Lys Pro Leu
        95                  100                 105

tgc gac ctg ctg atc cgc tgc atc aac tgc cag aag ccc ctg tgc ccc      385
Cys Asp Leu Leu Ile Arg Cys Ile Asn Cys Gln Lys Pro Leu Cys Pro
    110                 115                 120

gag gag aag cag cgc cac ctg gac aag aag cag cgc ttc cac aac atc      433
Glu Glu Lys Gln Arg His Leu Asp Lys Lys Gln Arg Phe His Asn Ile
125                 130                 135                 140

agg ggc cgg tgg acc ggg cgc tgc atg tcc tgc tgc cgc tcc tcc cgc      481
Arg Gly Arg Trp Thr Gly Arg Cys Met Ser Cys Cys Arg Ser Ser Arg
                145                 150                 155

acc cgc cgc gag acc cag ctg gac tac aag gac gac gac gac aag          526
Thr Arg Arg Glu Thr Gln Leu Asp Tyr Lys Asp Asp Asp Asp Lys
            160                 165                 170

taagaattcg gatccg                                                    542


<210> SEQ ID NO 2
<211> LENGTH: 171
<212> TYPE: PRT
<213> ORGANISM: Artificial Sequence
<220> FEATURE:
<223> OTHER INFORMATION: Synthetic Construct

<400> SEQUENCE: 2

Met His His His His His His Gln Lys Arg Thr Ala Met Phe Gln Asp
1               5                   10                  15

Pro Gln Glu Arg Pro Arg Lys Leu Pro Gln Leu Cys Thr Glu Leu Gln
            20                  25                  30

Thr Thr Ile His Asp Ile Ile Leu Glu Cys Val Tyr Cys Lys Gln Gln
        35                  40                  45

Leu Leu Arg Arg Glu Val Tyr Asp Phe Ala Phe Arg Asp Leu Cys Ile
    50                  55                  60

Val Tyr Arg Asp Gly Asn Pro Tyr Ala Val Cys Asp Lys Cys Leu Lys
65                  70                  75                  80

Phe Tyr Ser Lys Ile Ser Glu Tyr Arg His Tyr Cys Tyr Ser Leu Tyr
                85                  90                  95

Gly Thr Thr Leu Glu Gln Gln Tyr Asn Lys Pro Leu Cys Asp Leu Leu
            100                 105                 110

Ile Arg Cys Ile Asn Cys Gln Lys Pro Leu Cys Pro Glu Glu Lys Gln
        115                 120                 125

Arg His Leu Asp Lys Lys Gln Arg Phe His Asn Ile Arg Gly Arg Trp
    130                 135                 140

Thr Gly Arg Cys Met Ser Cys Cys Arg Ser Ser Arg Thr Arg Arg Glu
145                 150                 155                 160

Thr Gln Leu Asp Tyr Lys Asp Asp Asp Asp Lys
                165                 170


<210> SEQ ID NO 3
<211> LENGTH: 362
<212> TYPE: DNA
<213> ORGANISM: Artificial Sequence
<220> FEATURE:
<223> OTHER INFORMATION: Mutagenized E7 gene of HPV-16
<220> FEATURE:
<221> NAME/KEY: CDS
<222> LOCATION: (14)..(346)

<400> SEQUENCE: 3
```

-continued

```
caagcttgct agc atg cac cac cac cac cac cac ggc gac acc ccc acc        49
               Met His His His His His His Gly Asp Thr Pro Thr
               1               5                   10

ttg cac gag tac atg ttg gac ttg cag ccc gag acc acc gac ctg tac       97
Leu His Glu Tyr Met Leu Asp Leu Gln Pro Glu Thr Thr Asp Leu Tyr
        15                  20                  25

tgc tac gag cag ttg aac gac agc tcc gag gag gag gac gag atc gac      145
Cys Tyr Glu Gln Leu Asn Asp Ser Ser Glu Glu Glu Asp Glu Ile Asp
    30                  35                  40

ggc ccc gcc ggc cag gcc gag ccc gac cgc gcc cac tac aac atc gtg      193
Gly Pro Ala Gly Gln Ala Glu Pro Asp Arg Ala His Tyr Asn Ile Val
45                  50                  55                  60

acc ttc tgc tgc aag tgc gac tcc acc ctg cgc ctg tgc gtg cag agc      241
Thr Phe Cys Cys Lys Cys Asp Ser Thr Leu Arg Leu Cys Val Gln Ser
                65                  70                  75

acc cac gtg gac atc cgc acc ttg gag gac ctg ctg atg ggc acc ctg      289
Thr His Val Asp Ile Arg Thr Leu Glu Asp Leu Leu Met Gly Thr Leu
            80                  85                  90

ggc atc gtg tgc ccc atc tgc agc cag aag ccc gac tac aag gac gac      337
Gly Ile Val Cys Pro Ile Cys Ser Gln Lys Pro Asp Tyr Lys Asp Asp
        95                  100                 105

gac gac aag taagaattcg gatccg                                        362
Asp Asp Lys
    110


<210> SEQ ID NO 4
<211> LENGTH: 111
<212> TYPE: PRT
<213> ORGANISM: Artificial Sequence
<220> FEATURE:
<223> OTHER INFORMATION: Synthetic Construct

<400> SEQUENCE: 4

Met His His His His His His Gly Asp Thr Pro Thr Leu His Glu Tyr
1               5                   10                  15

Met Leu Asp Leu Gln Pro Glu Thr Thr Asp Leu Tyr Cys Tyr Glu Gln
            20                  25                  30

Leu Asn Asp Ser Ser Glu Glu Glu Asp Glu Ile Asp Gly Pro Ala Gly
        35                  40                  45

Gln Ala Glu Pro Asp Arg Ala His Tyr Asn Ile Val Thr Phe Cys Cys
    50                  55                  60

Lys Cys Asp Ser Thr Leu Arg Leu Cys Val Gln Ser Thr His Val Asp
65                  70                  75                  80

Ile Arg Thr Leu Glu Asp Leu Leu Met Gly Thr Leu Gly Ile Val Cys
                85                  90                  95

Pro Ile Cys Ser Gln Lys Pro Asp Tyr Lys Asp Asp Asp Asp Lys
            100                 105                 110


<210> SEQ ID NO 5
<211> LENGTH: 545
<212> TYPE: DNA
<213> ORGANISM: Artificial Sequence
<220> FEATURE:
<223> OTHER INFORMATION: Mutagenized E6 gene of HPV-18
<220> FEATURE:
<221> NAME/KEY: CDS
<222> LOCATION: (14)..(529)

<400> SEQUENCE: 5

caagcttgct agc atg cac cac cac cac cac cac gcc cgc ttc gag gac        49
               Met His His His His His His Ala Arg Phe Glu Asp
               1               5                   10
```

-continued ccc acc cgc cgc ccc tac aag ctg ccc gac ctg tgc acc gag ctg aac 97
Pro Thr Arg Arg Pro Tyr Lys Leu Pro Asp Leu Cys Thr Glu Leu Asn
15 20 25 acc tcc ctg cag gac atc gag atc acc tgc gtg tac tgc aag acc gtg 145
Thr Ser Leu Gln Asp Ile Glu Ile Thr Cys Val Tyr Cys Lys Thr Val
30 35 40 ctg gag ctg acc gag gtg ttc gag ttc gcc ttc aag gac ctg ttc gtg 193
Leu Glu Leu Thr Glu Val Phe Glu Phe Ala Phe Lys Asp Leu Phe Val
45 50 55 60 gtg tac cgc gac agc atc ccc cac gcc gcc tgc cac aag tgc atc gac 241
Val Tyr Arg Asp Ser Ile Pro His Ala Ala Cys His Lys Cys Ile Asp
65 70 75 ttc tac agc cgc atc cgc gag ctg cgc cac tac tcc gac tcc gtg tac 289
Phe Tyr Ser Arg Ile Arg Glu Leu Arg His Tyr Ser Asp Ser Val Tyr
80 85 90 ggc gac acc ctg gag aag ctg acc aac acc ggc ctg tac aac ctg ctg 337
Gly Asp Thr Leu Glu Lys Leu Thr Asn Thr Gly Leu Tyr Asn Leu Leu
95 100 105 atc cgc tgc ctg cgc tgc cag aag ccc ctg aac ccc gcc gag aag ctg 385
Ile Arg Cys Leu Arg Cys Gln Lys Pro Leu Asn Pro Ala Glu Lys Leu
110 115 120 cgc cac ctg aac gag aag cgc cgc ttc cac aac atc gcc ggc cac tac 433
Arg His Leu Asn Glu Lys Arg Arg Phe His Asn Ile Ala Gly His Tyr
125 130 135 140 cgc ggc cag tgc cac tcc tgc tgc aac cgc gcc cgc cag gag cgc ctg 481
Arg Gly Gln Cys His Ser Cys Cys Asn Arg Ala Arg Gln Glu Arg Leu
145 150 155 cag cgc cgc cgc gag acc cag gtg gac tac aag gac gac gac gac aag 529
Gln Arg Arg Arg Glu Thr Gln Val Asp Tyr Lys Asp Asp Asp Asp Lys
160 165 170 taagaattcg gatccg 545

<210> SEQ ID NO 6
<211> LENGTH: 172
<212> TYPE: PRT
<213> ORGANISM: Artificial Sequence
<220> FEATURE:
<223> OTHER INFORMATION: Synthetic Construct

<400> SEQUENCE: 6

Met His His His His His His Ala Arg Phe Glu Asp Pro Thr Arg Arg
1 5 10 15

Pro Tyr Lys Leu Pro Asp Leu Cys Thr Glu Leu Asn Thr Ser Leu Gln
20 25 30

Asp Ile Glu Ile Thr Cys Val Tyr Cys Lys Thr Val Leu Glu Leu Thr
35 40 45

Glu Val Phe Glu Phe Ala Phe Lys Asp Leu Phe Val Val Tyr Arg Asp
50 55 60

Ser Ile Pro His Ala Ala Cys His Lys Cys Ile Asp Phe Tyr Ser Arg
65 70 75 80

Ile Arg Glu Leu Arg His Tyr Ser Asp Ser Val Tyr Gly Asp Thr Leu
85 90 95

Glu Lys Leu Thr Asn Thr Gly Leu Tyr Asn Leu Leu Ile Arg Cys Leu
100 105 110

Arg Cys Gln Lys Pro Leu Asn Pro Ala Glu Lys Leu Arg His Leu Asn
115 120 125

Glu Lys Arg Arg Phe His Asn Ile Ala Gly His Tyr Arg Gly Gln Cys
130 135 140

-continued

```
His Ser Cys Cys Asn Arg Ala Arg Gln Glu Arg Leu Gln Arg Arg Arg
145                 150                 155                 160

Glu Thr Gln Val Asp Tyr Lys Asp Asp Asp Asp Lys
                165                 170


<210> SEQ ID NO 7
<211> LENGTH: 383
<212> TYPE: DNA
<213> ORGANISM: Artificial Sequence
<220> FEATURE:
<223> OTHER INFORMATION: Mutagenized E7 gene of HPV-18
<220> FEATURE:
<221> NAME/KEY: CDS
<222> LOCATION: (14)..(367)

<400> SEQUENCE: 7

caagcttgct agc atg cac cac cac cac cac cac ggc ccc aag gcc acc        49
               Met His His His His His His Gly Pro Lys Ala Thr
               1               5                   10

ctg cag gac atc gtg ctg cac ctg gag ccc cag aac gag atc ccc gtg       97
Leu Gln Asp Ile Val Leu His Leu Glu Pro Gln Asn Glu Ile Pro Val
        15                  20                  25

gac ctg ctg tgc cac gag cag ctg agc gac tcc gag gag gag aac gac      145
Asp Leu Leu Cys His Glu Gln Leu Ser Asp Ser Glu Glu Glu Asn Asp
    30                  35                  40

gag atc gac ggc gtg aac cac cag cac ctg ccc gcc cgc cgg gcc gag      193
Glu Ile Asp Gly Val Asn His Gln His Leu Pro Ala Arg Arg Ala Glu
45                  50                  55                  60

ccc cag cgc cac acc atg ctg tgc atg tgc tgc aag tgc gag gcc cgc      241
Pro Gln Arg His Thr Met Leu Cys Met Cys Cys Lys Cys Glu Ala Arg
                65                  70                  75

atc gag ctg gtg gtg gag agc tcc gcc gac gac ctg cgc gcc ttc cag      289
Ile Glu Leu Val Val Glu Ser Ser Ala Asp Asp Leu Arg Ala Phe Gln
            80                  85                  90

cag ctg ttc ctg aac acc ctg tcc ttc gtg tgc ccc tgg tgc gcc tcc      337
Gln Leu Phe Leu Asn Thr Leu Ser Phe Val Cys Pro Trp Cys Ala Ser
        95                  100                 105

cag cag gac tac aag gac gac gac gac aag taagaattcg gatccg            383
Gln Gln Asp Tyr Lys Asp Asp Asp Asp Lys
    110                 115


<210> SEQ ID NO 8
<211> LENGTH: 118
<212> TYPE: PRT
<213> ORGANISM: Artificial Sequence
<220> FEATURE:
<223> OTHER INFORMATION: Synthetic Construct

<400> SEQUENCE: 8

Met His His His His His His Gly Pro Lys Ala Thr Leu Gln Asp Ile
1               5                   10                  15

Val Leu His Leu Glu Pro Gln Asn Glu Ile Pro Val Asp Leu Leu Cys
            20                  25                  30

His Glu Gln Leu Ser Asp Ser Glu Glu Glu Asn Asp Glu Ile Asp Gly
        35                  40                  45

Val Asn His Gln His Leu Pro Ala Arg Arg Ala Glu Pro Gln Arg His
    50                  55                  60

Thr Met Leu Cys Met Cys Cys Lys Cys Glu Ala Arg Ile Glu Leu Val
65                  70                  75                  80

Val Glu Ser Ser Ala Asp Asp Leu Arg Ala Phe Gln Gln Leu Phe Leu
                85                  90                  95
```

-continued

```
Asn Thr Leu Ser Phe Val Cys Pro Trp Cys Ala Ser Gln Gln Asp Tyr
            100                 105                 110

Lys Asp Asp Asp Asp Lys
        115


<210> SEQ ID NO 9
<211> LENGTH: 1046
<212> TYPE: DNA
<213> ORGANISM: Artificial Sequence
<220> FEATURE:
<223> OTHER INFORMATION: HbsAG-EE7T Fusion protein
<220> FEATURE:
<221> NAME/KEY: CDS
<222> LOCATION: (29)..(1030)

<400> SEQUENCE: 9

ctcgaggatt ggggaccctg cgctgaac atg gag aac atc aca tca gga ttc        52
                               Met Glu Asn Ile Thr Ser Gly Phe
                               1               5

cta gga ccc ctt ctc gtg tta cag gcg ggg ttt ttc ttg ttg aca aga      100
Leu Gly Pro Leu Leu Val Leu Gln Ala Gly Phe Phe Leu Leu Thr Arg
    10                  15                  20

atc ctc aca ata ccg cag agt cta gac tcg tgg tgg act tct ctc aat      148
Ile Leu Thr Ile Pro Gln Ser Leu Asp Ser Trp Trp Thr Ser Leu Asn
25                  30                  35                  40

ttt cta ggg gga act acc gtg tgt ctt ggc caa aat tcg cag tcc cca      196
Phe Leu Gly Gly Thr Thr Val Cys Leu Gly Gln Asn Ser Gln Ser Pro
                45                  50                  55

acc tcc aat cac tca cca acc tct tgt cct cca act tgt cct ggt tat      244
Thr Ser Asn His Ser Pro Thr Ser Cys Pro Pro Thr Cys Pro Gly Tyr
            60                  65                  70

cgc tgg atg tgt ctg cgg cgt ttt atc atc ttc ctc ttc atc ctg ctg      292
Arg Trp Met Cys Leu Arg Arg Phe Ile Ile Phe Leu Phe Ile Leu Leu
        75                  80                  85

cta tgc ctc atc ttc ttg ttg gtt ctt ctg gac tat caa ggt atg ttg      340
Leu Cys Leu Ile Phe Leu Leu Val Leu Leu Asp Tyr Gln Gly Met Leu
    90                  95                  100

ccc gtt tgt cct cta att cca gga tcc tca aca acc agc acg gga cca      388
Pro Val Cys Pro Leu Ile Pro Gly Ser Ser Thr Thr Ser Thr Gly Pro
105                 110                 115                 120

tgc cgg acc tgc atg act act gct caa gga acc tct atg tat ccc tcc      436
Cys Arg Thr Cys Met Thr Thr Ala Gln Gly Thr Ser Met Tyr Pro Ser
                125                 130                 135

tgt tgc tgt acc aaa cct tcg gac gga aat tgc acc tgt att ccc atc      484
Cys Cys Cys Thr Lys Pro Ser Asp Gly Asn Cys Thr Cys Ile Pro Ile
            140                 145                 150

cca tca tcc tgg gct ttc gga aaa ttc cta tgg gag tgg gcc tca gcc      532
Pro Ser Ser Trp Ala Phe Gly Lys Phe Leu Trp Glu Trp Ala Ser Ala
        155                 160                 165

cgt ttc tcc tgg ctc agt tta cta gtg cca ttt gtt cag tgg ttc gta      580
Arg Phe Ser Trp Leu Ser Leu Leu Val Pro Phe Val Gln Trp Phe Val
    170                 175                 180

ggg ctt tcc ccc act gtt tgg ctt tca gtt ata tgg atg atg tgg tat      628
Gly Leu Ser Pro Thr Val Trp Leu Ser Val Ile Trp Met Met Trp Tyr
185                 190                 195                 200

tgg ggg cca agt ctg tac agc atc ttg agt ccc ttt tta ccg ctg tta      676
Trp Gly Pro Ser Leu Tyr Ser Ile Leu Ser Pro Phe Leu Pro Leu Leu
                205                 210                 215

cca att ttc ttt tgt ctt tgg gta tac att gat atc atg cac ggc gac      724
Pro Ile Phe Phe Cys Leu Trp Val Tyr Ile Asp Ile Met His Gly Asp
            220                 225                 230
```

-continued

```
acc ccc acc ttg cac gag tac atg ttg gac ttg cag ccc gag acc acc      772
Thr Pro Thr Leu His Glu Tyr Met Leu Asp Leu Gln Pro Glu Thr Thr
        235                 240                 245

gac ctg tac tgc tac gag cag ttg aac gac agc tcc gag gag gag gac      820
Asp Leu Tyr Cys Tyr Glu Gln Leu Asn Asp Ser Ser Glu Glu Glu Asp
    250                 255                 260

gag atc gac ggc ccc gcc ggc cag gcc gag ccc gac cgc gcc cac tac      868
Glu Ile Asp Gly Pro Ala Gly Gln Ala Glu Pro Asp Arg Ala His Tyr
265                 270                 275                 280

aac atc gtg acc ttc tgc tgc aag tgc gac tcc acc ctg cgc ctg tgc      916
Asn Ile Val Thr Phe Cys Cys Lys Cys Asp Ser Thr Leu Arg Leu Cys
                285                 290                 295

gtg cag agc acc cac gtg gac atc cgc acc ttg gag gac ctg ctg atg      964
Val Gln Ser Thr His Val Asp Ile Arg Thr Leu Glu Asp Leu Leu Met
            300                 305                 310

ggc acc ctg ggc atc gtg tgc ccc atc tgc agc cag aag ccc gac tac     1012
Gly Thr Leu Gly Ile Val Cys Pro Ile Cys Ser Gln Lys Pro Asp Tyr
        315                 320                 325

aag gac gac gac gac aag taagaattcg gatccg                           1046
Lys Asp Asp Asp Asp Lys
    330


<210> SEQ ID NO 10
<211> LENGTH: 334
<212> TYPE: PRT
<213> ORGANISM: Artificial Sequence
<220> FEATURE:
<223> OTHER INFORMATION: Synthetic Construct

<400> SEQUENCE: 10

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Met Thr Thr Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
```

-continued

```
    210                 215                 220

Tyr Ile Asp Ile Met His Gly Asp Thr Pro Thr Leu His Glu Tyr Met
225                 230                 235                 240

Leu Asp Leu Gln Pro Glu Thr Thr Asp Leu Tyr Cys Tyr Glu Gln Leu
                245                 250                 255

Asn Asp Ser Ser Glu Glu Glu Asp Glu Ile Asp Gly Pro Ala Gly Gln
            260                 265                 270

Ala Glu Pro Asp Arg Ala His Tyr Asn Ile Val Thr Phe Cys Cys Lys
        275                 280                 285

Cys Asp Ser Thr Leu Arg Leu Cys Val Gln Ser Thr His Val Asp Ile
    290                 295                 300

Arg Thr Leu Glu Asp Leu Leu Met Gly Thr Leu Gly Ile Val Cys Pro
305                 310                 315                 320

Ile Cys Ser Gln Lys Pro Asp Tyr Lys Asp Asp Asp Asp Lys
                325                 330
```

```
<210> SEQ ID NO 11
<211> LENGTH: 98
<212> TYPE: DNA
<213> ORGANISM: Artificial Sequence
<220> FEATURE:
<223> OTHER INFORMATION: Primer

<400> SEQUENCE: 11

ggatccaagc ttgccgtgat catgcacggc gacaccccca ccttgcacga gtacatgttg     60

gacttgcagc ccgagaccac cgacctgtac tgctacga                             98


<210> SEQ ID NO 12
<211> LENGTH: 79
<212> TYPE: DNA
<213> ORGANISM: Artificial Sequence
<220> FEATURE:
<223> OTHER INFORMATION: Primer

<400> SEQUENCE: 12

gtagtgggcg cggtcgggct cggcctggcc ggcggggccg tcgatctcgt cctcctcctc     60

ggagctgtcg ttcaactgc                                                  79


<210> SEQ ID NO 13
<211> LENGTH: 78
<212> TYPE: DNA
<213> ORGANISM: Artificial Sequence
<220> FEATURE:
<223> OTHER INFORMATION: Primer

<400> SEQUENCE: 13

gcccgaccgc gcccactaca acatcgtgac cttctgctgc aagtgcgact ccaccctgcg     60

cctgtgcgtg cagagcac                                                   78


<210> SEQ ID NO 14
<211> LENGTH: 95
<212> TYPE: DNA
<213> ORGANISM: Artificial Sequence
<220> FEATURE:
<223> OTHER INFORMATION: Primer

<400> SEQUENCE: 14

cccggggaat tccttagggc ttctggctgc agatggggca cacgatgccc agggtgccca     60

tcagcaggtc ctccaaggtg cggatgtcca cgtgg                                95
```

-continued

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
gacctgtact gctacgagca gttgaacgac agctccga 38

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16
aggtgcggat gtccacgtgg gtgctctgca cgca 34

<210> SEQ ID NO 17
<211> LENGTH: 60
<212> TYPE: DNA
<213> ORGANISM: Artificial Sequence
<220> FEATURE:
<223> OTHER INFORMATION: Primer

<400> SEQUENCE: 17
caagcttgct agcatgcacc accaccacca ccacggcgac acccccacct tgcacgagta 60

<210> SEQ ID NO 18
<211> LENGTH: 60
<212> TYPE: DNA
<213> ORGANISM: Artificial Sequence
<220> FEATURE:
<223> OTHER INFORMATION: Primer

<400> SEQUENCE: 18
caagcttgct agcatgcacc accaccacca ccacgacgag atcgacggcc ccgccggcca 60

<210> SEQ ID NO 19
<211> LENGTH: 66
<212> TYPE: DNA
<213> ORGANISM: Artificial Sequence
<220> FEATURE:
<223> OTHER INFORMATION: Primer

<400> SEQUENCE: 19
cggatccgaa ttcttacttg tcgtcgtcgt ccttgtagtc gggcttctgg ctgcagatgg 60
ggcaca 66

<210> SEQ ID NO 20
<211> LENGTH: 6
<212> TYPE: PRT
<213> ORGANISM: Artificial
<220> FEATURE:
<223> OTHER INFORMATION: Hexa-His-Tag

<400> SEQUENCE: 20

His His His His His His
1 5

<210> SEQ ID NO 21
<211> LENGTH: 8
<212> TYPE: PRT

-continued

<213> ORGANISM: Artificial Sequence
<220> FEATURE:
<223> OTHER INFORMATION: Flag-tag

<400> SEQUENCE: 21

Asp Tyr Lys Asp Asp Asp Asp Lys
1 5

<210> SEQ ID NO 22
<211> LENGTH: 15
<212> TYPE: DNA
<213> ORGANISM: Artificial Sequence
<220> FEATURE:
<223> OTHER INFORMATION: Primer

<400> SEQUENCE: 22
ctcgaggatt gggga 15

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
gatatcaatg tatacccaaa ga 22

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
gatatcgagg aggacgagat cga 23

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
gatatcatgc acggcgaca 19

<210> SEQ ID NO 26
<211> LENGTH: 715
<212> TYPE: DNA
<213> ORGANISM: Artificial Sequence
<220> FEATURE:
<223> OTHER INFORMATION: Synthetic gene EHBs Ag-S-F

<400> SEQUENCE: 26
ctcgaggatt ggggaccctg cgctgaacat ggagaacatc acctccggct tcctgggccc 60
cctgctggtg ctgcaggccg gcttcttcct gctgacccgc atcctgacca tcccccagag 120
cctggactcc tggtggacct ccctgaactt cctgggcggc accaccgtgt gcctgggcca 180
gaactcccag tcccccacct ccaaccactc ccccacctcc tgcccccca cctgccccgg 240 ctaccgctgg atgtgcctgc gccgcttcat catcttcctg ttcatcctgc tgctgtgcct 300
gatcttcctg ctggtgctgc tggactacca gggcatgctg cccgtgtgcc ccctgatccc 360

-continued

```
cggctccagc accaccagca ccggcccctg ccgcacctgc atgaccaccg cccagggcac    420

ctccatgtac ccctcctgct gctgcaccaa gcccagcgac ggcaactgca cctgcatccc    480

catccccagc tcctgggcct tcggcaagtt cctgtgggag tgggccagcg cccgcttcag    540

ctggctgagc ctgctggtgc ccttcgtgca gtggttcgtg ggcctgagcc ccaccgtgtg    600

gctgagcgtg atctggatga tgtggtactg ggccccagc ctgtacagca tcctgagccc    660

cttcctgccc ctgctgccca tcttcttctg cctgtgggtg tacatcgata tctaa         715


<210> SEQ ID NO 27
<211> LENGTH: 227
<212> TYPE: PRT
<213> ORGANISM: Artificial Sequence
<220> FEATURE:
<223> OTHER INFORMATION: Synthetic gene EHBs Ag-S-F

<400> SEQUENCE: 27

Met Glu Asn Ile Thr Ser Gly Phe Leu Gly Leu Leu Val Leu Gln Ala
1               5                   10                  15

Gly Phe Phe Leu Leu Thr Arg Ile Leu Thr Ile Pro Gln Ser Leu Asp
                20                  25                  30

Ser Trp Trp Thr Ser Leu Asn Phe Leu Gly Gly Thr Thr Val Cys Leu
        35                  40                  45

Gly Gln Asn Ser Gln Ser Pro Thr Ser Asn His Ser Pro Thr Ser Cys
    50                  55                  60

Pro Pro Thr Cys Pro Gly Tyr Arg Trp Met Cys Leu Arg Arg Phe Ile
65                  70                  75                  80

Ile Phe Leu Phe Ile Leu Leu Leu Cys Leu Ile Phe Leu Leu Val Leu
                85                  90                  95

Leu Asp Tyr Gln Gly Met Leu Pro Val Cys Pro Leu Ile Pro Gly Ser
            100                 105                 110

Ser Thr Thr Ser Thr Gly Pro Cys Arg Thr Cys Met Thr Thr Ala Gln
        115                 120                 125

Gly Thr Ser Met Tyr Pro Ser Cys Cys Cys Thr Lys Pro Ser Asp Gly
    130                 135                 140

Asn Cys Thr Cys Ile Pro Ile Pro Ser Ser Trp Ala Phe Gly Lys Phe
145                 150                 155                 160

Leu Trp Glu Trp Ala Ser Ala Arg Phe Ser Trp Leu Ser Leu Leu Val
                165                 170                 175

Pro Phe Val Gln Trp Phe Val Gly Leu Ser Pro Thr Val Trp Leu Ser
            180                 185                 190

Val Ile Trp Met Met Trp Tyr Trp Gly Pro Ser Leu Tyr Ser Ile Leu
        195                 200                 205

Ser Pro Phe Leu Pro Leu Leu Pro Ile Phe Phe Cys Leu Trp Val Tyr
    210                 215                 220

Ile Asp Ile
225
```

MODIFIED HPV E6 AND E7 GENES AND PROTEINS USEFUL FOR VACCINATION

CROSS-REFERENCE TO RELATED APPLICATIONS

This application is filed under the provisions of 35 U.S.C. §371 and claims the priority of International Patent Application No. PCT/ep02/03271 filed 22 Mar. 2002, which in turn claims priority of European Patent Application No. 01107271.7 filed 23 Mar. 2001.

BACKGROUND OF THE INVENTION

1. Field of the Invention

The present invention relates to DNA sequences encoding an E6 or E7 fusionprotein of HPV, wherein said DNA sequences are characterized by a combination of the following features: original codons are exchanged by codons which lead to an enhanced translation in a mammalian cell, they contain a deletion resulting in the production of a truncated non-functional protein, and they encode a fusion-partner which is a highly immunogenic polypeptide capable of enhancing the immunogenicity of the E6- or E7-protein in the mammalian host. Furthermore, this invention relates to the modified E6- or E7-protein encoded by said DNA sequences as well as expression vectors containing said DNA sequences. Finally, the present invention relates to several uses of the above compounds, particularly as effective vaccines useful in treatment or prevention of an HPV infection or a neoplasm associated with HPV infection.

2. Description of Related Art

Carcinoma of the uterine cervix (cervical cancer, CC) is the second most common cancer in women worldwide and the first in developing countries. CC develops through premalignant intermediate stages of increasing severity known as cervical intraepithelial neoplasia (CIN) grades 1–3, the latter leading to the development of invasive cancer in about 50% of cases over a period of 1–2 decades. More than 11% of the global cancer incidence in women is due to human papillomavirus (HPV) infections. Infection with HPV types 16 and 18 has been associated with the development of CIN and CC, with HPV genotype 16 being the most prevalent viral type to infect the cervix. The E6 and E7 proteins encoded by these HPV types are thought to be involved in the pathogenesis of CC by inducing abnormal cell proliferation. Expression of E6 and E7 is consistently detected in tissue and tumor cells from HPV-associated CCs. Furthermore, the E6 and E7 genes from HPV types 16 and 18 are sufficient for transformation of epithelial cells in culture (zur Hausen, Biochim. Biophys. Acta 1288(2) (1996): F55–78).

There is increasing evidence that the E6 and E7 proteins encoded by HPV types 16 and 18 may be effective immunological targets for tumor rejection by the host. Efforts are being made to develop effective preventive and therapeutic vaccines which may be useful in treatment and prevention of a neoplasm associated to HPV. The different strategies employed so far for inducing an immune responses to proteins of the HPV types 16 and 18 are: (a) Use of synthetic antigenic peptides, (b) Use of recombinant microorganisms (recombinant bacille Calmette-Guerin; BCG), (c) use of DNA vaccines using wild-type viral genes and (d) use of Virus-like particles (VLPs).

However, unfortunately, the above strategies exhibit a variety of disadvantages which so far have hampered the development of a safe and efficient vaccine. As regards the use of synthetic antigenic peptides it has to be stressed that the identification of HPV specific, immunoreactive peptides is very complex. It requires large numbers and quantities of peptides for vaccines to be effective and of a broad spectrum. Moreover, synthetic peptides do not contain posttranslational modifications (e.g., glycosylation, sulfation, phosphorylation) normally found in native proteins and therefore are not efficient enough as vaccines. The BCG based vaccine delivery systems expressing the L1 late protein of HPV 6b or the E7 early protein of HPV 16 have been used as immunogens. However, the immune responses obtained with these systems was even less than those elicited by protein/adjuvant vaccines and, thus, this system is considered unlikely to be useful as a single component vaccine strategy. As regards DNA vaccines it has been observed that the expression of wild-type HPV genes is quite low, even if they are expressed from strong promoters, such as that of the cytomegalovirus (CMV). As regards the use of Virus-like particles (VLPs) it has to be mentioned that true VLPs are made of the L1 (capsid) protein of a specific HPV type. Therefore, they may be only useful as prophylactic rather than as therapeutic vaccines, if ever. Pseudotyped VLPs containing, for instance, epitopes of HPV-16 E7 have also been described and may be useful as prophylactic and therapeutic vaccines. However, an important limitation is that VLPs are produced in insect cells or in yeast. So far, no suitable production systems in mammalian cells have been established. Therefore critical epitopes depending on post-translational modifications which take place in human cells are lost in these systems.

Therefore, it is the object of the present invention to provide a safe and effective vaccine, preferably a genetic vaccine, for the treatment or prevention of an HPV infection or a neoplasm associated to HPV.

SUMMARY OF THE INVENTION

According to the invention this is achieved by the subject matters defined in the claims. The present invention provides DNA sequences for inducing immune response to the E6 and/or E7 proteins of oncogenic HPV in a host animal, preferably by administering vectors containing said DNA sequences, e.g. plasmid vectors, herpes simplex virus type 1 amplicon or recombinant Semliki forest virus vectors. Said DNA sequences encode the HPV proteins as fusion proteins that are immunogenic but are not capable of inducing cell transformation. The DNA sequences of the invention are characterized bay the following features:

(a) The DNA sequences of the HPV E6/E7 genes have been modified to make their codon usage closer to that of human genes, (b) the genes have been modified by deletion to make them non-functional, thereby disabling their oncogenic capability (deletions are, preferably, point mutations, because these lead to loss of potentially essential epitopes), (c) the HPV genes have been fused to highly immunogenic proteins to enhance their immunogenicity in the host (these fusions are not expected to result in masking of HPV protein epitopes, since the fragments fused are of sufficient length as to avoid this problem), and, preferably, expression of the HPV genes is provided by recombinant, replication-deficient HSV, SFV or high copy plasmid vectors or combinations of these.

This approach offers a variety of advantages, namely:

(a) Higher expression levels of the HPV protein as a result of the silent mutations introduced in the HPV genes to make their codon usage closer to the human are obtained.

This results in a more efficient host response in immunization trials compared to the use of wild-type HPV genes.

(b) The HPV genes and proteins generated by the present invention are expressed in human cells and, unlike proteins expressed in other systems such as bacteria, yeast or insect cells, they contain posttranslational modifications normally found in proteins expressed in human cells. This is crucial for an adequate recognition of the HPV proteins by the host immune system.

(c) Since the HPV proteins are expressed fused to proteins known to be highly immunogenic, they elicit stronger immune responses in the host animal.

(d) The HPV proteins are not cell-transforming neither in vitro nor in the host animal because in no case are they expressed as full-length polypeptides. The HPV fusion genes express incomplete proteins, whose functions are impaired. In addition, the HPV proteins are expressed as fusions to cytoplasmic proteins and therefore they can not reach the nucleus where they exert their functions.

(e) The HPV proteins are, preferably, expressed tagged with a specific sequence, which can be easily detected in Western blots and by immunofluorescence with the help of commercially available antibodies.

(f) The combination of various viral vectors and of these with plasmid vectors ensures a more efficient immunization, since it prevents neutralization of the vector by immune reaction elicited in a previous boost.

DETAILED DESCRIPTION OF THE INVENTION

Accordingly, the present invention relates to a DNA sequence encoding an E6 or E7 fusionprotein of HPV, wherein said DNA sequence is characterized by a combination of the following features:

(a) at least 20% of the original codons are exchanged by codons which lead to an enhanced translation in a mammalian cell;

(b) it contains a mutation resulting in the production of a truncated non-functional protein; and (c) it encodes a fusionpartner which is a highly immunogenic polypeptide capable of enhancing the immunogenicity of the E6 or E7 protein in the mammalian host.

The expression “orignial codons” refers to the codons found in the corresponding wildtype version of the HPV.

The expression “enhanced translation in a mammalian cell” refers to the genes resulting from introduction of silent mutations in the HPV sequences, as described in the present invention, which create open reading frames consisting entirely of preferred human codons, and thus lead to enhanced expression of the proteins they encode in mammalian cells.

The term “mutation resulting in the production of a truncated non-functional protein” refers to any mutation which leads to the production of a non-functional version of the protein. Preferably, such a mutation leads to a truncated version of the protein. Examples of appropriate mutations include a mutation, wherein at least one codon has been deleted or a mutation leading to premature termination of translation. Such mutation is, e.g., the replacement of a codon encoding a particular amino acid by a stop codon, an insertion or deletion of one or two nucleotides resulting in a frame shift mutation etc. The term “non-functional protein or gene” means that the mutant HPV genes and proteins of the present invention are “nontransforming neither in vitro nor in vivo” meaning that the capability of the E6 or E7 genes and proteins to transform cells to a tumorigenic phenotype has been eliminated as demonstrated by standard tests. The person skilled in the art can easily determine whether a particular mutation leads to an E6 or E7 gene or protein with the desired characteristics, i.e. which is “non-transforming” according to standard procedures. These include:

1) In vitro: Transformation assays of NIH 3T3 cells and primary human keratinocytes. Transforming genes (oncogenes) have been routinely identified by use of assays in which transformed foci result from transfection of tumor or recombinant DNA into NIH 3T3 cells (Todaro et al., PNAS USA 51: 66–73, 1964; Jainchill et al., J. Virol. 4: 549–553, 1969; Andersson et al., Cell 16: 63–75, 1979). These cells are murine fibroblasts maintained as contact-inhibited, non-tumorigenic cell lines. Transfer of DNA containing an activated oncogene will occasionally give rise to foci of morphologically altered cells that have tumorigenic properties.

2) In vivo: Tumorigenicity tests are routinely performed in immunodeficient mice by inoculation with mouse or human transformed cells. Cells transfected to express HPV E6 and E7 genes and cell lines derived from cervical carcinomas infected by HPV, such as HeLa cells, have been shown to be tumorigenic (Lichy et al., Cell Growth Differ.3: 541–548, 1992; Stanbridge, Nature 260: 17–20, 1976).

In a preferred embodiment, the DNA sequence of the present invention encodes the HPV E7 protein with the above described characteristics.

In a further preferred embodiment, at least 50% of the original codons of the DNA sequence of the present invention are replaced by codons which lead to an enhanced translation in a mammalian cell; examples of suitable replacements are e.g., shown in FIGS. 1 and 2, SEQ ID NO: 3 and 1, respectively.

In a further preferred embodiment, the DNA sequence of the present invention contains a frame-shift point mutation leading to premature stop of translation.

The person skilled in the art knows polypeptides or parts thereof which are suitable as fusionpartner for the E6 or E7 protein and which are highly immunogenic in mammals, particularly in humans. Examples of suitable polypeptides include:

1) Hepatitis B virus small envolope protein (HBsAg—S). This protein has the capacity to self-assemble with host-derived membranes to form empty subviral particles, which are released into the lumen of a pre-Golgi compartment and subsequently secreted (Ganem, “Hepadnaviridae and their replication” p2703–37, in Fields, Knipe and Howley (eds.), Fields Virology 3$^{rd}$ ed., 1996, Lippincott-Raven Publishers, Philadelphia). E6 or E7 can be fused to the C-terminus of the protein which remains exposed on the surface of the subviral particles.

2) E2 glycoprotein of Semliki forest virus (SFV). E2 is a spike component of the SFV virion and a major antigen for neutralizing antibodies (Schlesinger and Schlesinger, “Togaviridae: the viruses and their replication” in Fields, Knipe and Howley (eds.), Fields Virology 3$^{rd}$ ed., 1996, Lippincott-Raven Publishers, Philadelphia). E6 or E7 can be fused to the N-terminus of the E2 protein that is exposed on the surface of the viral envelope or the plasma membrane of E2-expressing cells.

3) Human amyloid β-protein precursor (APP). APP is a transmembrane protein with a large extracellular region and a small cytoplasmic tail. It is normally cleaved by protease to yield a 40 amino acid β-peptide (amyloid), which is found in the plaques of patients with Alzheimer’s disease, or a smaller fragment called p3, which may associate with extracellular matrix ("Principles of neural Science", Kandel, Schwartz, and Jessell, (eds.) $3^{rd}$ ed., 1991, Elsevier, N.Y.). E6 and E7 can be inserted into the extracellular part of APP and are thought to be released together with the β-peptide or the p3 fragment.

4) Human chromogranin B (hCgB). Although hCgB is a protein involved in the regulated secretory pathway, it has been shown to be constitutively secreted in cells without a regulated pathway, such as HeLa cells, upon transfection (Kaether, and Gerdes, FEBS Letters 369: 267–271, 1995). E6 or E7 can be fused to the C-terminus of hCgB.

5) The bacterial β-galactosidase, known to be highly immunogenic (Fijikawa et. al., Virology 204: 789–793, 1994). E6 or E7 can be fused to the N-or the C-terminus of the protein. As the fusion product is a soluble non-membrane protein that may diffuse to the nucleus, E6 or E7 is a deletion (inactive) mutant. Alternatively, a signal peptide is added to the fusion which targets the product to the cell surface.

6) Fusion of the N-or C-terminal halves of E6 or E7 together and the resulting chimeric polypeptide fused to any of the above proteins.

The present invention particularly, but not exclusively, relates to the E6 and E7 genes and proteins of the HPV-16 and HPV-18 genotypes. It will be, however, appreciated that the invention extends to variants of such HPV genotypes and other HPV genotypes which may have oncogenic or other pathologic potential.

In a preferred embodiment, the present invention relates to chimeric genes encoding a polyprotein containing E6 and E7 of HPV-16 and E6 and E7 of HPV-18, either complete or as deletion fragments comprising N- or C-terminal halves of such proteins, fused together and to the polypeptides or parts thereof mentioned above. This allows immunization against HPV16 and HPV18 using a single product as immunogen.

Persons skilled in the art will appreciate that the fusion of E6 and/or E7 to the proteins 1–4 of the above list abolishes the translocation of the former to the nucleus, thus interfering with their function. Further, secretion or surface exposure of the fusion proteins is intended to facilitate their recognition by the immune system.

In a particular preferred embodiment, the present invention relates to a DNA sequence wherein parts (a) and (b) comprise the coding region of the DNA sequence as depicted in FIG. 1 (SEQ ID NO: 3), 2 (SEQ ID NO: 1), 3 (SEQ ID NO: 7) or 4 (SEQ ID NO: 5 3) including the Flag-tag or not. Even more preferred is an embodiment of the DNA sequences of the present invention, which comprises the coding region of the DNA sequence as depicted in FIG. 5 (SEQ ID NO: 9) including the Flag-tag or not.

Preferably, the mutant HPV E6 and E7 proteins encoding DNA sequences are present in a vector or expression vector. A person skilled in the art is familiar with examples thereof. In the case of an expression vector for *E. coli* these are e.g. pGEMEX, pUC derivatives, pGEX-2T, pET3b, T7 based expression vectors and pQE-8. For the expression in yeast, e.g. pY100 and Ycpad1 have to be mentioned while e.g. pKCR, pEFBOS, cDM8, pMSCND, and pCEV4 have to be indicated for the expression in animal cells. The baculovirus expression vector pAcSGHisNT-A is especially suitable for the expression in insect cells. The DNA sequences of the present invention can also be contained in a recombinant virus containing appropriate expression cassettes. Suitable viruses that may be used in the present invention include baculovirus, vaccinia, sindbis virus, SV40, Sendai virus, adenovirus, an AAV virus or a parvovirus, such as MVM or H-1. The vector may also be a retrovirus, such as MoMULV, MoMuLV, HaMuSV, MuMTV, RSV or GaLV. Particular preferred plasmids and recombinant viruses are piRES—Neo2 (Clontech, Heidelberg, Deutschland), pTet-On (Clontech), pHSVPUC (Geller et al., PNAS USA 87 (1990), 8950–8954), HSV amplicons and recombinant SFV vectors. For expression in mammals, the DNA sequences of the invention are operatively linked to a suitable promoter, e.g. a human cytomegalovirus "immediate early promoter" (pCMV), SV40 enhancer and early promoter, SRα promoter (Takebe et al., Mol. Cell. Biol. 8: 466–472, 1988), Tet-On/Tet-Off gene expression systems, immediate early E4/5 promoter of HSV-1 (Geller et al., PNAS USA 87: 8950–8954, 1990).

For generating E6 and E7 protein encoding DNA sequences carrying the above discussed modifications and for constructing expression vectors which contain the DNA sequences according to the invention, it is possible to use general methods known in the art. These methods include e.g. in vitro recombination techniques, synthetic methods and in vivo recombination methods as described in Sambrook et al., Molecular Cloning, A Laboratory Manual, $2^{nd}$ edition (1989) Cold Spring Harbor Laboratory Press, Cold Spring Harbor, N.Y., for example.

Furthermore, the present invention relates to host cells which contain the above described DNA sequences or vectors. These host cells include bacteria, yeast, insect and animal cells, preferably mammalian cells. The *E. coli* strains HB101, DH1, x1776, JM101, JM109, BL21, XL1Blue and SG 13009, the yeast strain *Saccharomyces cerevisiae*, the insect cells sf9 and the animal cells L, A9, 3T3, FM3A, BHK, human SW13, CHO, COS, Vero and HeLa are preferred. Methods of transforming these host cells, of phenotypically selecting transformants and of expressing the DNA according to the invention by using the above described vectors are known in the art.

The present invention also relates to an HPV E6 or E7 protein which is encoded by the above described DNA sequences. The HPV E6 or E7 protein is provided as isolated, purified material, and therefore free of other proteins. Such HPV proteins are, preferably, expressed in human cells and, unlike proteins expressed in other systems such as bacteria, yeast or insect cells, they contain the posttranslational modifications normally found in the proteins expressed in human cells. This may be of decisive importance for an adequate recognition of the HPV proteins by the host immune system.

Furthermore, the present invention relates to a method of producing the above E6 or E7 protein, whereby, e.g., a host cell of the invention is cultivated under conditions allowing the synthesis of the protein and the protein is subsequently isolated from the cultivated cells and/or the culture medium. Isolation and purification of the recombinantly produced proteins may be carried out by conventional means including preparative chromatography and affinity and immunological separations involving affinity chromatography with monoclonal or polyclonal antibodies.

The present invention also relates to a pharmaceutical composition comprising a DNA sequence or an expression vector of the invention or, alternatively, the HPV E6 or E7 protein encoded by said DNA sequence in a pharmaceutically acceptable carrier.

Finally, the present invention relates to various uses of the DNA sequences of the invention, expression vectors or HPV E6 or E7 proteins. Preferred uses are:

(a) Preparation of a vaccine for the prevention or treatment of a HPV infection or a neoplasm associated with HPV infection. Preferably, the vaccine is a genetic vaccine based on the DNA sequences of the invention inserted into an appropriate vector under the control of a suitable promoter, e.g. a vector or promoter as described above. Such a vaccine can be used to stimulate humoral and/or cellular immune response in subjects who may benefit from such responses by protection against or treatment of possible infections by HPV or by rejection of cells from tumors or lesions which are infected by HPV and express viral proteins.

(b) Production of polyclonal or monoclonal antibodies which might be useful as therapeutic agents. Such antibodies can be generated according to well known methods.

(c) Detection of specific antibodies or cytotoxic T lymphocytes in subjects infected by HPV, i.e. use in a diagnostic assay. Suitable assay formats (RIA, ELISA etc.) are well known to the person skilled in the art.

(d) Generation of a transgenic mouse line using, e.g., the DNA sequences of the invention under the control of a tetracycline inducible promoter. Such mouse line might be useful to test vaccines against HPV.

BRIEF DESCRIPTION OF THE DRAWINGS

FIG. 1: HPV16 EE7T-sequence

The nucleotide sequence (SEQ ID NO: 3) and derived amino acid sequence (SEQ ID NO: 4) (single-letter code) of the mutagenized E7 gene of HPV-16 (EE7T) is shown. Silent mutations which were introduced to create an open reading frame of preferred human codons are denoted in bold. The sequences encoding the hexa-His-tags and Flag-tags are underlined. The stop codon is denoted by an asterisk.

FIG. 2: HPV16 EE7T-sequence

The nucleotide sequence (SEQ ID NO: 1) and derived amino acid sequence (SEQ ID NO: 2) (single-letter code) of the mutagenized E6 gene of HPV-16 (EE6T) is shown. Silent mutations which were introduced to create the open reading frame of preferred human codons are denoted in bold. The sequences encoding the hexa-His-tags and Flag-tags are underlined. The stop codon is denoted by an asterisk.

FIG. 3: HPV18 EE7T-sequence

The nucleotide sequence (SEQ ID NO: 7) and derived amino acid sequence (SEQ ID NO: 8) (single-letter code) of the mutagenized E7 gene of HPV-18 (EE7T) is shown. Silent mutations which were introduced to create the open reading frame of preferred human codons are denoted in bold. The sequences encoding the hexa-His-tags and Flag-tags are underlined. The stop codon is denoted by an asterisk.

FIG. 4: HPV18 EE6T-sequence

The nucleotide sequence (SEQ ID NO: 5) and derived amino acid sequence (SEQ ID NO: 6) (single-letter code) of the mutagenized E6 gene of HPV-18 (EE6T) is shown. Silent mutations which were introduced to create the open reading frame of preferred human codons are denoted in bold. The sequences encoding the hexa-His-tags and Flag-tags are underlined. The stop codon is denoted by an asterisk.

FIG. 5: HbsAg-EE7T Fusion Gene

The nucleotide sequence (SEQ ID NO: 9) and derived amino acid sequence (SEQ ID NO: 10) (singleletter code) of the HbsAg-EE7T fusion gene is shown. The fused fragments are separated by three dots. Silent mutations which were introduced into the E7 gene of HPV-16 (EE7T) to convert the open reading frame of preferred human codons are denoted in bold. The sequence encoding the Flag-tag is underlined. The stop codon is denoted by an asterisk.

Figure 6:
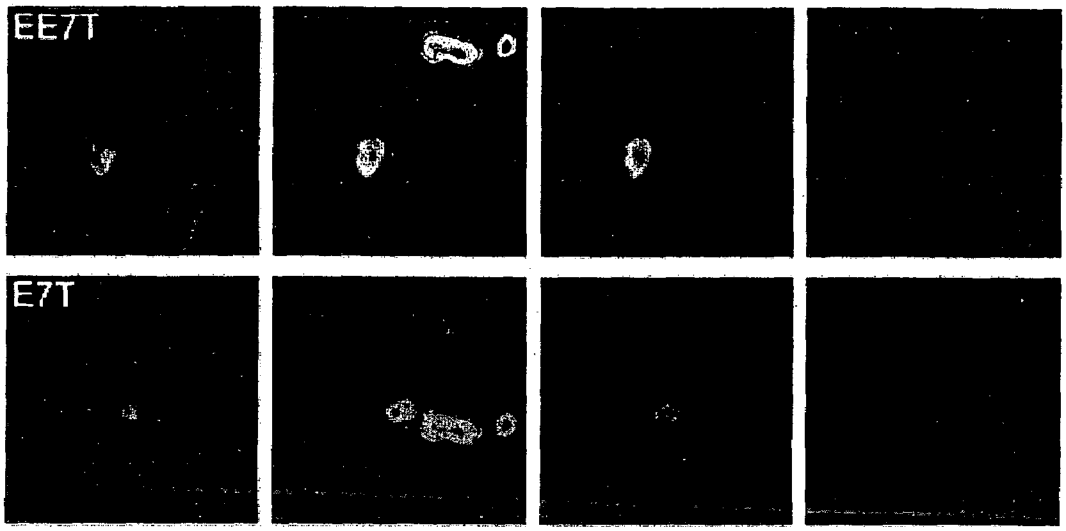

FIG. 6: Confocal image analysis of expression of the HPV-16 E7 fusion proteins encoded by the mutant genes EE7T and E7T Vero cells growing on coverslips were transfected with either plasmid pIRES-Neo2/EE7T or pIRES-Neo2/E7T using the “FuGene” transfection reagent (Roche, Basel Schweiz). The cells were incubated for 48 h, fixed with 2% paraformaldehyde, permeabilized with 0.2% Triton X-100 and stained by sequential incubations with anti-Flag M2 monoclonal antibodies (Sigma-Aldrich, Steinheim, Deutschland and goat anti-mouse antibodies conjugated to cy2 (Dianova, Hamburg, Deutschland).

Figure 7:
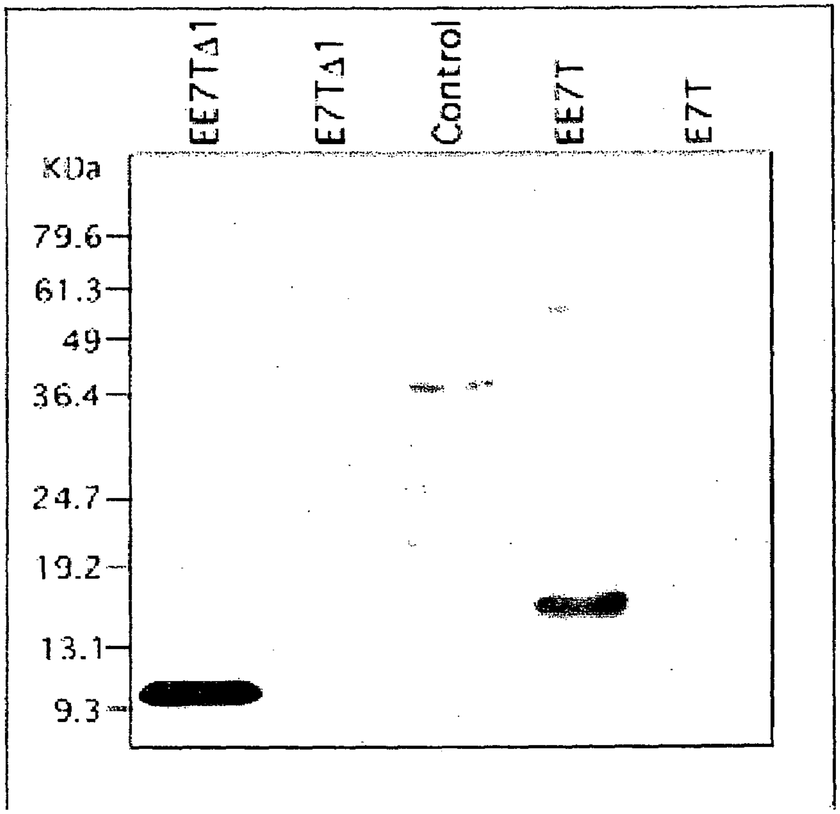

FIG. 7 Western blot analysis of expression of the HPV-16 E7 fusion proteins encoded by the EE7T and E7T genes HeLa cells were transfected as described in FIG. 6. After 24 h cells were lysed in SDS buffer, proteins separated by PAGE (15% polyacrylamide), transferred to PVDF membranes Immobilion-P, Millipore, Eschborn, Deutschland) and hybridized with anti-Flag M2 monoclonal antibodies conjugated to horse-radish peroxidase, which activity was detected by ECL assay.

FIG. 8: Sequence of the synthetic EHBsAg-S-F gene and its translation

Silent mutations introduced to create an open reading frame of preferred human codons are denoted in uppercase characters. The sequence of the Eco RV site is underlined. The aminoacid sequence (SEQ ID NO: 27) is given below the nucleotide sequence (SEQ ID NO: 26) according to the one-letter code.

FIG. 9: Sequence of the EHBsAg-S-16EE7T fusion gene

The first codon of EE7T is underlined. (SEQ ID NOs: 9 and 10)

Figure 10:
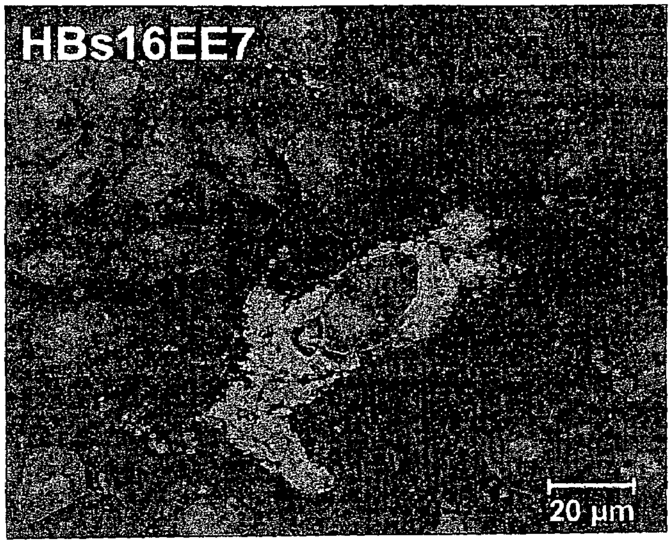

FIG. 10: Immunofluorescence of Vero cells transfected with pIN-EHBsAg-S-EE7T The cells were lysed 48 h after transfection, fixed with 4% paraformaldehyde, permeabilized with 0.1% (v/v) Triton X-100 in PBS and blocked. Immunodetection of the EHBsAg-S-EE7T fusion protein was carried out using an anti-Flag M2 antibody (Sigma), followed by a Cy2 (green) conjugated anti-mouse antibody (Molecular Probes). The nuclei were counterstained with propidium iodide.

Figure 11:
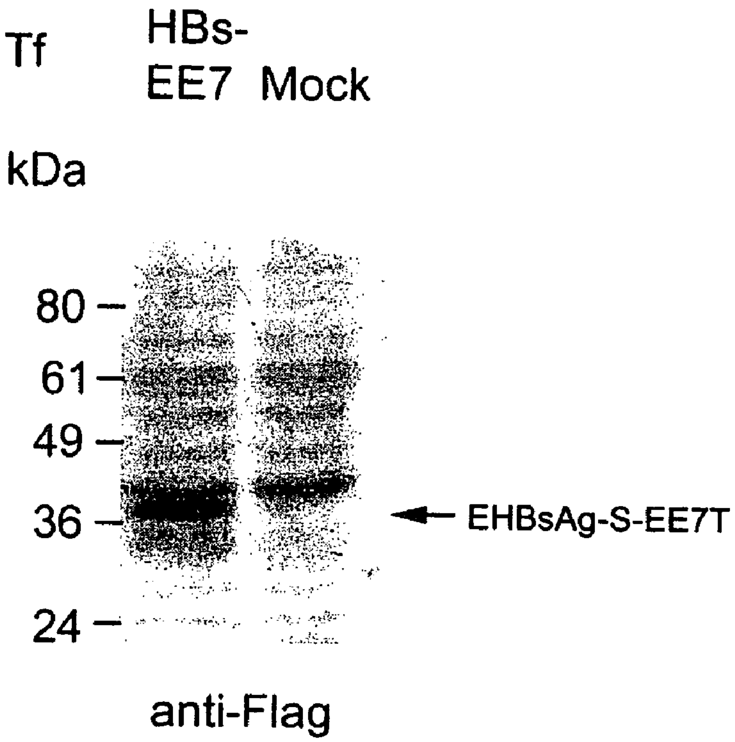

FIG. 11: Western blot analysis of Vero cells transfected with pIN-EHBsAg-S-EE7T The cells were lysed 48 h after transfection and equal amounts of extract were loaded onto a 10% SDS-acrylamide gel. After transfer to a PVDF membrane and blocking, immunodetection was carried out with anti-Flag M2 antibody conjugated to horseradish peroxidase (Sigma).

Figure 12:
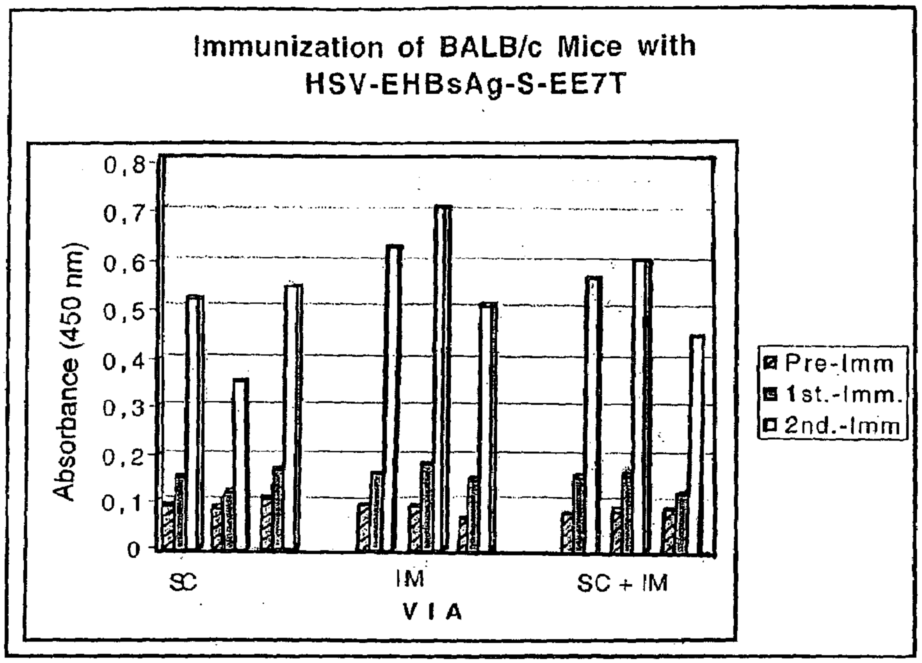

FIG. 12: Immunogenicity of the EHBsAg-S-16EE7T fusion protein tested in BALB/c mice.

The present invention is explained by the examples.

EXAMPLE 1

Mutagenesis and Expression of the E7 Gene of HPV Type 16

The HPV-16 E7 gene was mutagenized in vitro to introduce 64 silent mutations which create an open reading frame comprised of preferred human codons. In addition, the mutant E7 genes were fused to a hexa-histidine-tag and a Flag-tag.

The mutant E7 genes were synthetically produced by sequential steps of polymerase-chain-reaction (PCR) using the following primers:

```
(a) 5'-GGA TCC AAG CTT GCC GTG ATC ATG CAC GGC GAG ACC CCC ACC  (SEQ ID NO: 11)
    TTG CAC GAG TAC ATG TTG GAC TTG CAG CCC GAG ACC ACC GAG CTG
    TAC TGC TAG GA-3'
(b) 5'-GTA GTG GGC GCG GTC GGG CTC GGC CTG GCC GGC GGG GCC      (SEQ ID NO: 12)
    GTC GAT CTC GTC CTC CTC CTC GGA GCT GTC GTT CAA CTG C-3'
(c) 5'-GCC CGA CCG CGC CCA CTA CAA CAT CGT GAC CTT CTG CTG      (SEQ ID NO: 13)
    CAA GTG CGA CTC CAC CCT GCG CCT GTG CGT GCA GAG CAC-3'
(d) 5'-CCC GGG GAA TTC CTT AGG GCT TCT GGC TGC AGA TGG GGC      (SEQ ID NO: 14)
    ACA CGA TGC CCA GGG TGC CCA TCA GCA GGT CCT CCA AGG TGC GGA
    TGT CCA CGT GG-3'
(e) 5'-GAC CTG TAC TGC TAC GAG CAG TTG AAC GAC AGC TCC GA-3'   (SEQ ID NO: 15)
(f) 5'-AGG TGC GGA TGT CCA CGT GGG TGC TCT GCA CGC A-3'        (SEQ ID NO: 16)
(g) 5'-CAA GCT TGC TAG CAT GCA CCA CCA CCA CCA CCA CGG CGA CAC  (SEQ ID NO: 17)
    CCC CAC CTT GCA CGA GTA-3'
(h) 5'-CAA GCT TGC TAG CAT GCA CCA CCA CCA CCA CCA CGA CGA GAT  (SEQ ID NO: 18)
    CGA CGG CCC CGC CGG CCA-3'
(i) 5'-CGG ATC CGA ATT CTT ACT TGT CGT CGT CGT CCT TGT AGT CGG  (SEQ ID NO: 19)
    GCT TCT GGC TGC AGA TGG GGC ACA-3'
```

In the first PCR step, primers (b) and (e) (PCR1) and primers (c) and (f) (PCR2) were used to generate the respective fragments by chain extension using no template. In a second step, the products of PCR1 and PCR2 were utilized to amplify a single fragment using no primers (PCR3). In a third step, the product of PCR3 was used as template to amplify a complete E7 gene with primers (a) and (d) (PCR4).

In a final PCR step, the product of PCR4 (EE7) was utilized as template to amplify the following : (1) by using primers (g) and (i) a complete E7 sequence fused to sequences encoding an hexa-His-tag (HHHHHH-epitope) (SEQ ID NO: 20) at its N-terminus, and a Flagtag (DYKD-DDDK-epitope) (SEQ ID NO: 21) at its C-terminus was synthesized (enhanced E7 with tags: EE7T); (2) by using primers (h) and (i) a truncated E7 (EE7T□1) lacking the first 35 residues, which contains His- and Flag-tags as described above was synthesized.

The mutated tagged E7 genes were isolated from the PCR reaction mixtures by agarose gel electrophoresis, double digested with NheI and EcoRI and cloned into the multiple cloning site of the plasmid pIRES-Neo2 (Clontech, Heidelberg, Deutschland) digested previously with the same restriction enzymes. After transformation of DH5α bacteria, single clones were identified and sequenced. Clones with the correct sequence were expanded and used to purify the corresponding plasmids. As control, a wild-type E7 gene and a truncated mutant lacking the first 35 residues, both tagged in the same way as the EE7T mutants described above, were cloned by PCR (E7T and E7TΔ1 genes), and subsequently inserted in the Nhel and EcoRI sites of the pIRES-Neo2 plasmid.

The EE7 product from PCR4 was also cloned in pBluescript-vector (Stratagene, Amsterdam, Niederlande) and used for mutagenesis which resulted in a double deletion mutant lacking residues 26–32 and 70–74. The EE7 product from PCR4 was used as template for amplification as follows: (1) by using primers (g) and (i) an EE7T deletion mutant lacking residues 26–32 and 70–74 (EE7TΔ2,3), with His- and Flag-tags as above was generated, (2) by using primers (h) and (i) a truncated EE7T lacking the first 35 residues as well as residues 70–74 (EE7TΔ1,3), with His- and Flag-tags as above was generated.

EXAMPLE 2

Expression of EE7T Fusion Genes in Mammalian Cells

The expression of the EE7T fusion genes described in Example 1, above, was tested in vitro by immunofluorescence and Western blot analysis as compared to that of the E7T controls. The above plasmids were used for transient transfection using eukaryotic cell lines of mouse (C-26), monkey (Vero 2-2), and human (HeLa) origin. The cell line Vero 2-2 contains the HSV-1 IE2 (ICP27) gene and promoter. This line was originally established by R. M. Sandri-Goldin et al. (Smith et al., Virology 186 (1992), 74–86). At different times of expression the cells were fixed with paraformaldehyde and processed for immunodetection or were lysed in SDS loading buffer and analyzed by Western blot. In both cases the E7 fusion proteins were detected with mouse monoclonal antibodies specific for the hexa-His (anti-His-tag Ab-1, Calbiochem-Novabiochem, Bad Soden, Deutschland) or the Flag epitopes (anti-Flag M2, Sigma-Alderich, Steinheim, Deutschland).

Image analysis of Immunofluorescence preparations showed expression of the mutant proteins in the nucleus of the transfected cells (FIG. 6). Western blots probed with monoclonal antibodies directed against the Flag epitope showed that expression of mutagenized E7 genes (EE7 and its deletion mutants described above) was at least two orders of magnitude higher than that of equivalent E7 genes made of wild-type codons (VE7 and its deletion mutants) (FIG. 7).

EXAMPLE 3

Cloning and Expression of E7 /HBsAg Fusion Genes

In order to enhance the antigenic potential of E7, fusion proteins were created between tagged EE7 open reading frames and a gene encoding the surface antigen of hepatitis B virus (HbsAg). The fusion gene was created by PCR cloning of the HbsAg and the EE7 genes. Plasmid pRc/CMV-HBs(S) (Aldevron, Fargo, USA) served as template to amplify the HbsAg gene using the primers 5'-CTC GAG GAT TGG GGA-3' (SEQ ID NO: 22) and 5'-GAT ATC AAT GTA TAC CCA AAG A-3' (SEQ ID NO: 23). The resulting fragment contains the full sequence of the HbsAg open reading frame except for the termination codon, which was replaced by an EcoRV site. The mutant EE7T genes were amplified using as template the full-length EE7 gene described in Example 1 and as primers for the 5'-end the oligonuoleotides 5'-GAT ATC GAG GAG GAC GAG ATC GA-3' (SEQ ID NO: 24) or 5'-GAT ATC ATG CAC GGC GAC A-3' (SEQ ID NO: 25) and for the 3'-end the oligonucleotide (i) described in Example 1. The EE7T genes amplified in this way were cut with EcoRV and ligated to the 3'-end of the HbsAg generated above to produce HbsAg-EE7T fusion genes expressing either the complete EE7 gene or the EE7T□1 or □ deletion mutants.

The HbsAg-EE7T fusion genes were cloned into the polylinker of the plasmid pIRESNeo2 and used for transient transfection using eukaryotic cell lines of mouse (C-26; tumor library, DKFZ, Heidelberg, Germany), monkey (Vero 2-2), and human (HeLa) origin.

EXAMPLE 4

1. Transformation Studies of the Enhanced HPV Genes.

Experimental evidence has accumulated demonstrating that E6 and E7 from HPV16 and HPV18 have tansforming potential. When expressed under the control of strong heterologous promoters, these genes have been shown to transform established mouse cells (Kanda et al., J. Viol. 62: 610–613, 1988; Vousden et al., Oncogene Res. 3:167–175, 1989) and to immortalize primary murine and human foreskin keratinocytes (Halbert et al., J. Virol. 65:473–478, 1991; Hudson et al., J. Virol. 64: 519–526, 1990; Sedman et al., J. Virol. 65:4860–4866).

The transforming potential of the enhanced genes of the present invention and of their derivatives (fusion proteins like that of FIGS. 5 and others in which the HPV gene has a deletion of at least 50 %) was tested by standard methods using mouse NIH 3T3 cells and primary human keratinocytes. Their wild type counterparts and empty plasmid vector were used as positive and negative controls, respectively.

The HPV enhanced genes and their fusion DNA constructs were subcloned into the multiple cloning site of the plasmid pIRESNeo2 (Clontech, Heidelberg, Deutschland). The resulting plasmids were amplified in *E.coli* and purified on resin (Quiagen, Hilden, Deutschland), eluted, ethanol precipitated and resuspended in sterile, deionized water. DNA quanitity and purity was determined by spectrophotometric measurements of absorbance at 260 and 280 nm and by agarose gel electrophoresis. NIH 3T3 cells (ATCC, Manassas) were maintained on Dulbecco's modified Eagle's medium supplemented with L-glutamine and 10% fetal calf serum Transfection of NIH 3T3 cells with plasmid DNA was carried out using FuGene™ 6 Transfection Reagent (Roche, Mannheim, Deutschland) essentially as described by the manufacturer. Cells seeded at 3×10 in a 100 mm dish were transfected the following day with 3 μg of test plasmid. Each transfection was done in triplicate. After 48 h incubation at 37° C., transfected cells were removed by trypsinization and either assayed for colony formation in soft agar or subcultured into three 100 mm dishes and incubated for further 24 h at 37° C. before selection was performed in medium containing Geneticin (Life Technologies, Karlsruhe, Deutschland) at a concentration of 500 μg/ml. For assays of colony formation in soft agar, trypsinized cells were seeded into 0.4% agar in growth medium at $10^5$ cells per 60 mm dish and incubated at 37° C. Duplicate dishes were scored for colony formation after two weeks. Neomycin resistant colonies were selected by addition of Geneticin to subconfluent cell monolayers, the cells were trypsinized and assayed for colony formation in soft agar as described above.

Transfection of primary human keratinocytes with plasmid DNA was carried out using FuGene™ 6 Transfection Reagent as above. Keratinocytes were grown in KGM medium (KMK2 kit, Sigma-Aldrich, Steinheim, Deutschland) in 30 mm dishes. Cells were transfected at passage 5 with 5 μg DNA. After approaching confluence, the cultures were split at a ration of 1:2 and selection with 100 μg of Geneticin per ml was carried out.

All HPV enhanced fusion genes tested failed to produce foci of NIH 3T3 cells in soft agar and to immortalize primary human keratinocytes.

2. Immunogenicity Sudies of the Enhanced HPV Genes.

The enhanced HPV genes were subcloned into the plasmid pHSVPUC (Geller et al., PNAS USA87: 8950–8954, 1990) and the resulting recombinant constructs used to generate amplicon HSV-1 vectors as described elsewhere (Cid-Arregui, and Lim, in Cid-Arregui and Garcia (eds), "Viral Vectors: Basic Science and Gene Therapy", BioTechniques Books, Eaton Publishing, Natick), and these used for immunization studies in BALB/c mice. Groups of five mice (8 weeks old, female) were used for each immunization experiment. On day 0, $10^{3-104}$ virus particles in a 50 μl suspension in saline serum were inoculated subcutaneously. At day 14, a second dose of the formulation was applied in the same way. At day 28, the mice were bled.

Serum antibody responses to E6 and E7 were measured using plates coated with recombinant E6 or E7 protein using standard procedures. Sera were diluted in PBS pH 7.2 containing 1 mg/ml casein, 0.5% Tween 20, 0.002% alphazurine A.

After washing the plates, 0.1 ml/well of test serum at the appropriate dilution was added, and the plates incubated for 1 h at 38° C. To detect bound antibody, 0.1 ml of 0.1 μg/ml of horseradish peroxidase-labeled goat anti-mouse IgG+IgM (H and L chain specific) in PBS pH 7.2 supplemented as above was added. The plates were incubated for 1 h at 20° C. and washed 6 times with PBS pH 7.2 with 0.5% Tween 20. Then 0.1 ml of substrate TMB (3,3', 5,5'tetramethylbenzidine, Sigma-Aldrich, Steinheim, Deutschland) was added. Following 10 min of incubation at 20° C., the reaction was stopped by addition of 50 μl of 0.5 M $H_2SO_4$. Colorimetric measurements were performed in a vertical beam spectrophotometer at 450 nm.

All mice immunized with vectors expressing enhanced HPV E6 and E7 genes separately or as fusion genes as described in the present invention produced a significant response following immunization which was clearly higher than that elicited by the non-enhanced controls.

EXAMPLE 5

Generation of a Synthetic EHBsAg-S-Fusion Gene

The hepatitis B virus (HBV) small antigen (HBsAg-S) is an envelope protein with the capacity to self-assemble with cell-derived lipid membranes into empty particles without the participation of nucleocapsids. These subviral particles are produced as spherical or filamentous forms of 22 nm in diameter, which bud into the lumen of a pre-Golgi compartment and are subsequently secreted as cargo. It is believed that subviral particles induce a more effective immune response than denatured or soluble viral proteins. Furthermore, they can not replicate and are noninfectious.

This example describes the development of recombinant HBsAg-S particles containing B- and T-cell epitopes of the E6 and/or E7 genes of oncogenic genital HPV types fused to the C-terminus of HBsAg-S, and the humoral immune response induced by these particles in mice.

1. Generation and Expression of a Synthetic HBsAg-S Gene

A synthetic HBsAg-S gene was generated in vitro, which contains 155 silent mutations that create an open reading frame entirely comprised of preferred human codons. Two extra codons (GATATC) were added just preceding the stop codon which create an Eco RV restriction site that allows for fusion of genes starting with an Eco RV site in frame at their 5' end. The resulting gene was named EHBsAg-S-F (Enhanced HBsAg for Fusion).

The synthetic EHBsAg-S-F gene was produced by successive steps of polymerase-chain-reaction (PCR) using the following oligonucleotides:

(1) EH1 (forward)

5' CTC GAG GAT TGG GGA CCC TGC GCT GAA Cat gga gaa cat (SEQ ID NO: 28)

cac Ctc Cgg Ctt cct Ggg Ccc cct Gct Ggt gCT Gca ggc Cgg

Ctt Ct 3'

(2) EH2 (anti-parallel)

5' tCa gGg aGg tcc acc aGg agt cCa gGc tct gGg gGa tGg (SEQ ID NO: 29)

tCa gga tGc GGg tca Gca Gga aGa aGc cGg cct gCA Gca cCa gCa 3'

(3) EH3 (forward)

5' tGg act cCt ggt gga cCt cCc tGa aCt tCc tGg gCg gCa (SEQ ID NO: 30)

cCa ccg tgt gCc tGg gcc aGa aCt cCc agt ccc cCa cct cca aCc a 3'

(4) EH4 (anti-parallel)

5' aGc gGc gca gGc aca tcc agc gGt aGc cGg gGc aGg tGg (SEQ ID NO: 31)

gGg gGc aGg agg tGg gGg agt gGt tgg agg tGg ggg act gGg aGt t 3'

(5) EH5 (forward)

5' taC cgc tgg atg tgC ctg cgC cgC ttC atc atc ttc ctG (SEQ ID NO: 32)

ttc atc ctg ctg ctG tgc ctG atc ttc Ctg Ctg gtG ctG ctg gac t 3'

(6) EH6 (anti-parallel)

5' aGg gGc cGg tgc tgg tGg tGC Tgg aGc cGg gGa tCa gGg (SEQ ID NO: 33)

gGc aCa cgg gca Gca tGc cCt gGt agt cca gCa gCa cca Gca

Gga aga t (7) EH7 (forward)

tcc AGC acC acc agc acC ggC ccC tgc cgC acc tgc atg acC (SEQ ID NO: 34)

acC gcC caG ggC acc tcC atg taC ccc tcc tgC tgc tgC a 3'

(8) EH8 (anti-parallel)

-continued

```
5' tGc cga aGg ccc agg aGC TGg gga tgg gGa tGc agg tgc     (SEQ ID NO: 35)

aGt tGc cgt cGC TGg gCt tgg tGc agc aGc agg agg gGt aca

tGg a 3'

(9) EH9 (forward)

5' atc ccC AGC tcc tgg gcC ttc ggC aaG ttc ctG tgg gag     (SEQ ID NO: 36)

tgg gcc AGC gcc cgC tt cAG Ctg gct Gag CCt Gct Ggt gcc

Ctt Cgt 3'

(10) EH10 (anti-parallel)

5' acc aca tca tcc aGa tCa cGC TCa gcc aCa cGg tgg ggC     (SEQ ID NO: 37)

TCa gGc cCa cga acc act gCa cGa aGg gca cCa gCa GGc tCa

gcc a 3'

(11) EH11 (forward)

5' tGA GCg tGa tCt gga tga tgt ggt aCt ggg gCc cCa gCc     (SEQ ID NO: 38)

tgt aca gca tcC tga gCc cct tCC tG ccC ctg Ct 3'

(12) EH12 (anti-parallel)

5' tta GAT ATC Gat gta Cac cca Cag Gca Gaa gaa Gat Ggg     (SEQ ID NO: 39)

CaG cag Ggg CaG Gaa ggg Gct caG ga 3'
```

The synthetic EHBsAg-F gene was generated through four PCR steps as follows:

In a first step, primers EH1 and EH2 (for PCR 1A), EH3 and EH4 (for PCR 1B), EH5 and EH6 (for PCR 1C), EH7 and EH8 (for PCR 1D), EH9 and EH10 (for PCR 1E), and primers EH11 and EH12 (for PCR 1F) were used to generate fragments by chain extension using no template.

In a second step, the products of PCR 1A and 1B (for PCR 2A), 1C and 1D (for PCR 2B), and 1E and 1F (for PCR 2C) were utilized to amplify unique fragments using primers EH1 and EH4 (PCR 2A), EH5 and EH8 (PCR 2B), and EH9 and EH12 (PCR 2C).

In a third step, the products of PCR 2A and 2B were used to amplify a unique fragment (PCR 3) without using primers.

In a final PCR step, the product of PCR 3 and 2C were mixed and used to amplify a unique fragment (PCR 4) using primers EH1 and EH12.

The resulting full length EHBsAg-S-F gene (715 base pairs in length, FIG. 8) (SEQ ID NO: 26) was isolated from the PCR reaction mixture by agarose gel electrophoresis, purified and cloned into a unique Eco RV site in the polylinker of the pIRES-Neo2 plasmid (Clontech). The resulting plasmid (pIN-EHBsAg-S-F) was purified from DH5α bacteria, and the sequence of the EHBSAg-F gene verified by DNA sequencing using primers hybridizing upstream and downstream the polylinker.

Expression of the EHBsAg-S-F gene was tested by immunofluorescence and Western blot analysis of transiently transfected cells. To this end, the plasmid pIN-EHBsAg-F was transfected into eukaryotic cell lines of mouse (C-26), monkey (Vero 2-2), and human (HeLa) origin using Effectene™ (Qiagen) or FuGene™ (Roche) . At different times of expression (24 and 48 h) the cells were fixed with paraformaldehyde and processed for immunofluorescence or lysed in SDS loading buffer and analyzed by Western blot. In both cases the EHBsAg-S-F protein (SEQ ID NO: 27) was detected using mouse monoclonal antibodies specific for HBsAg-S (Aldevron)

Image analysis of Immunofluorescence preparations showed expression of the HBsAg proteins in the Golgi compartments of transfected cells. Western blots probed with monoclonal antibodies to HBsAg showed expression levels about 5–10 times higher using the EHBsAg-S gene than when the wild-type HBsAg-S gene was used for transfection.

2. Generation of Synthetic EHBsAg-S Fusion Genes

Fusions of the EHBsAg-S-F with synthetic HPV genes were generated following the strategy described below for the EE7T synthetic gene described in Example 1 and shown in FIG. 3. The HPV-16 EE7T genes containing an Eco RV site at their 5'-end were amplified from the pIRESNeo2/EE7T plasmid by PCR using the following primers:

```
1) 167HLF5': 5' GAT ATC ATG CAC GGC GAC A 3'                          (SEQ ID NO: 40)

2) 167HSF5': 5' GAT ATC GAG GAG GAC GAG ATC GA 3'                     (SEQ ID NO: 41)

3) 167HL3a:  5' CGG ATC CGA ATT CTT ACT TGT CGT CGT CGT CCT TGT AGT (SEQ ID NO: 42)

             CGG GCT TCT GGC TGC AGA TGG GGC ACA 3'
```

The pair of primers 167HLF5' and 167HL3a served to amplify a full length EE7T. The pair 167HSF5' and 167HL3a was used to amplify a truncated EE7T gene lacking the first 35 codons (EE7TΔ1). The resulting fragments were sequentially treated with T4-DNA polymerase, T4-polynucleotide kinase, restricted with Eco RV and purified using Qiaex II (Qiagen). Finally, the fragments were inserted, separately, into the plasmid pIN-EHBsAg-S-F cut with Eco RV and Stu I. The sequence of the resulting fusion (plasmids pIN-EHBsAg-S-EE7T and pIN-EHBsAg-S-16EE7T, FIG. 9, and pIN-EHBsAg-S-16EE7T?1, respectively) was verified by sequencing.

Expression of the EHBsAg-S-16EE7T genes was tested by immunofluorescence and Western blot analysis of transiently transfected cells. The plasmids pIN-EHBsAg-S-16EE7T and pIN-EHBsAg-S-16EE7T?l were transfected separately into eukaryotic cell lines of mouse (C-26), monkey (Vero 2-2), and human (HeLa) origin using Effecten™ (Qiagen) or FuGene™ (Roche). At different times of expression (24 and 48 h) the cells were fixed with paraformaldehyde and processed for immunofluorescence (FIG. 10) or lysed in SDS loading buffer and analyzed by Western blot. In both cases the EHBsAg-S-16EE7T proteins were detected using mouse monoclonal antibodies specific for HBsAg-S (Aldevron) and anti-flag antibodies (M2 mAb, Sigma) (FIG. 11).

3. Immunization of Mice with Synthetic EHBsAg-S-16EE7T Fusion Genes

Immunogenicity of the EHBsAg-S-16EE7T fusion protein was tested in BALB/c mice. On day 0, eight groups of three mice (10–12 weeks old, females) were inoculated with $10^4$ infectious units of herpes simplex amplicon expressing EHBsAg-S-16EE7T in 40 μl of buffer TN (50 mM Tris-HCl pH7.4, 100 mM NaCl, 0.5 mM EDTA) either subcutaneously (dorsal, close to the head), intramuscularly (Tibialis anterior muscle) or both subcutaneously and intramuscularly. A second dose was administered to all groups on day 15.

All mice were bled at days 15 and 25. Serum antibody responses to EHBsAg-S-16EE7T were measured by EIA. Nunc 96-multiwell plates were coated with recombinant HBsAg-S protein by incubating 0.1 ml/well for 2 h at 37° C. of a 10 μg/ml in 4M urea in 50 mM carbonate buffer pH 9.5. The buffer was aspirated and the plates incubated at 37° C. for 1 h with 0.2 ml/well of 1 mg/ml of casein in PBS pH 7.2. The plates were then washed six times with PBS pH 7.2, 0.5% (v/v) Tween 20. Test sera, diluted in PBS pH 7.2, 0.5% (v/v) Tween 20, 1 mg/ml of casein, were added and the plates incubated for 1 h at 37° C. The plates were then washed six times with PBS pH 7.2, 0.5% (v/v) Tween 20. Bound antibody was detected by adding 0.1 ml/well of 0.1 μg/ml of horseradish peroxidase labelled goat anti-mouse IgG+IgM in PBS pH 7.2, 0.5% (v/v) Tween 20, 1 mg/ml of casein. The plates were incubated for 1 h at 20° C., washed six times with PBS pH 7.2, 0.5% (v/v) Tween 20, a nd incubated for 10 min with 0.1 ml of enzyme substrate (3,3',5,5'-tetramethylbenzidine/$H_2O_2$). The reaction was stopped by addition of 50 μl of 0.5 M $H_2SO_4$. Color was measured at 450 nm in a plate reader (FIG. 12).

The invention claimed is:

1. A DNA sequence encoding an E7 fusion protein of HPV, wherein said DNA sequence is characterized by a combination of the following features:

(a) at least 20% of the original codons are exchanged by codons which lead to an enhanced translation in a mammalian cell;

(b) it contains a mutation resulting in the production of a truncated non-functional protein; and (c) it encodes a fusion partner which is an immunogenic polypeptide capable of enhancing the immunogenicity of the E7 protein in the mammalian host;

wherein said DNA sequence comprises the coding region of the DNA sequence as depicted in SEQ ID NO: 9 including the Flag-tag or not.

2. The DNA sequence of claim 1, wherein at least 50% of the original codons are replaced by codons which lead to an enhanced translation in a mammalian cell.

3. The DNA sequence of claim 1, wherein the mutation is a frame-shift point mutation leading to premature stop of translation.

4. The DNA sequence of claim 1, wherein the fusion partner is HbsAg or an immunogenic part thereof.

5. The DNA sequence of claim 1, wherein the DNA sequence includes a Flag-tag.

6. The DNA sequence of claim 1, wherein the DNA sequence does not include a Flag-tag.

7. A pharmaceutical composition comprising a DNA sequence according to claim 1.

8. An expression vector containing a DNA sequence of claim 1.

9. The expression vector of claim 8, which is a plasmid or a recombinant virus.

10. The expression vector of claim 9, wherein the plasmid or recombinant virus is pIRES-Neo2, pTet-On, pHSVPUC, an HSV amplicon or a SFV vector.

11. A host cell containing the DNA sequence according to claim 1.

12. A host cell containing the expression vector of claim 8.

13. A host cell containing the expression vector of claim 9.

14. A host cell containing the expression vector of claim 10.

15. A method of producing an E7 protein, comprising introducing an expression vector according to claim 8 in a host cell and culturing of the host cell under suitable conditions to express the E7 protein.

16. A method of treating an HPV infection or a neoplasm associated to HPV infection, the method comprising administering to a subject in need of treatment a vaccine comprising a DNA sequence according to claim 1.

17. A method for the production of a polyclonal or monoclonal antibody, comprising use of an E7 protein encoded by a DNA sequence according to claim 1 for the production of said polyclonal or monoclonal antibody.

18. A method for the detection of specific antibodies or cytotoxic T lymphocytes in subjects infected by HPV, comprising use of an E7 protein encoded by a DNA sequence according to claim 9 in an assay for the detection of specific antibodies or cytotoxic T lymphocytes in said subjects infected by HPV.

19. A method for the generation of a transgenic mouse line, comprising use of a DNA sequence according to claim 1.

* * * * *